(12) United States Patent
Ferrara et al.

(10) Patent No.: US 7,371,377 B2
(45) Date of Patent: May 13, 2008

(54) ANTIBODIES TO POLYPEPTIDES HOMOLOGOUS TO VEGF AND BMP1

(75) Inventors: Napoleone Ferrara, San Francisco, CA (US); Sophia S. Kuo, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 574 days.

(21) Appl. No.: 10/178,442

(22) Filed: Jun. 19, 2002

(65) Prior Publication Data

US 2003/0113870 A1 Jun. 19, 2003

Related U.S. Application Data

(60) Division of application No. 09/265,686, filed on Mar. 10, 1999, now Pat. No. 6,455,283, which is a continuation-in-part of application No. 09/184,216, filed on Nov. 2, 1998, now abandoned, which is a continuation-in-part of application No. 09/040,220, filed on Mar. 17, 1998, now Pat. No. 6,391,311.

(51) Int. Cl.
C07K 16/00 (2006.01)
A61K 39/395 (2006.01)

(52) U.S. Cl. .............................. 424/130.1; 530/388.1; 530/388.23; 530/389.1; 530/389.2; 530/387.9; 530/387.1; 530/387.3; 424/133.1; 424/139.1; 424/141.1; 424/158.1

(58) Field of Classification Search ..................... None
See application file for complete search history.

(56) References Cited

U.S. PATENT DOCUMENTS

| | | | |
|---|---|---|---|
| 4,816,567 A * | 3/1989 | Cabilly et al. ........... 530/387.3 |
| 4,877,864 A | 10/1989 | Wang et al. |
| 5,013,649 A | 5/1991 | Wang et al. |
| 5,106,748 A | 4/1992 | Wozney et al. |
| 5,166,058 A | 11/1992 | Wang et al. |
| 5,332,671 A * | 7/1994 | Ferrara et al. ............. 435/360 |
| 5,399,677 A | 3/1995 | Wolfman et al. |
| 5,453,419 A | 9/1995 | Murakami et al. |
| 5,543,394 A | 8/1996 | Wozney et al. |
| 5,620,867 A | 4/1997 | Kiefer et al. |
| 5,631,142 A | 5/1997 | Wang et al. |
| 5,637,480 A | 6/1997 | Celeste et al. |
| 5,641,756 A | 6/1997 | Robinson |
| 5,661,007 A | 8/1997 | Wozney et al. |
| 5,670,338 A | 9/1997 | Murakami et al. |
| 6,391,311 B1 | 5/2002 | Ferrara et al. |
| 6,455,283 B1 | 9/2002 | Ferrara et al. |
| 6,620,784 B1 | 9/2003 | Ferrara et al. |
| 6,887,982 B1 * | 5/2005 | Gao et al. ................. 530/387.9 |
| 2003/0027998 A1 | 2/2003 | Holtzman et al. |
| 2004/0138417 A1 * | 7/2004 | Fitzpatrick et al. ......... 530/350 |
| 2004/0219640 A1 | 11/2004 | Ferrara et al. |
| 2004/0235740 A1 | 11/2004 | Ferrara et al. |
| 2007/0031929 A1 | 2/2007 | Ferrara |

FOREIGN PATENT DOCUMENTS

| | | |
|---|---|---|
| EP | 471754 B1 | 7/1996 |
| EP | 370989 B1 | 9/1996 |
| WO | WO 88/00205 | 1/1988 |
| WO | WO 94/01548 | 1/1994 |
| WO | WO 96/30046 | 10/1996 |
| WO | WO 98/07832 | 2/1998 |
| WO | WO 98/45332 | 10/1998 |
| WO | WO 99/37671 | 7/1999 |
| WO | WO99/46281 | 9/1999 |
| WO | WO 99/47677 | 9/1999 |
| WO | WO 00/04183 | 1/2000 |
| WO | WO 00/24774 | 4/2000 |
| WO | WO 00/18212 | 6/2000 |
| WO | WO 00/32221 | 6/2000 |
| WO | WO 00/34474 | 6/2000 |
| WO | WO 00/37641 | 6/2000 |
| WO | WO 00/39284 | 7/2000 |
| WO | WO 00/53758 | 9/2000 |
| WO | WO 00/59940 | 10/2000 |
| WO | WO 00/66736 | 11/2000 |

OTHER PUBLICATIONS

Einhorn, M.D. Lawrence H., "Charles F. Kettering Prize. Clinical trails in testicular cancer" *Cancer* 71(10) :3182-3184 (May 15, 1993).
Lyttle, D. et al., "Homologs of vascular endothelial growth factor are encoded by the poxvirus orf virus" *Journal of Virology* 68(1) :84-92 (Jan. 1994).
Presta, L. et al., "Humanization of anti-vascular endothelial growth factor monoclonal antibody for the therapy of solid tumors and other disorders" *Cancer Research* 57(20) :4593-4599 (Oct. 15, 1997).
Remadi, S. et al., "Metastasizing placental site trophoblastic tumor: immunohistochemical and DNA analysis. 2 case reports and a review of literature" *Archives of Gynecology and Obstetrics* 259(2) :97-103 (1997).
Yoshida, S. et al., "Involvement of interleukin-8, vascular endothelial growth factor, and basic fibroblast growth factor in tumor necrosis factor alpha-dependent angiogenesis" *Molecular & Cellular Biology* 17(7) :4015-4023 (Jul. 1997).
"EMBL Database Accession No. AA631149".
Achen et al., "Vascular endothelial growth factor D (VEGF-D) is a ligand for the tyrosine kinases VEGF receptor 2 (Flk1) and VEGF receptor 3 (Flt4)" *Proc. Natl. Acad. Sci. USA* 95(2):548-553 (Jan. 20, 1998).

(Continued)

*Primary Examiner*—Marianne P Allen
(74) *Attorney, Agent, or Firm*—Carol A. Fang

(57) ABSTRACT

The present invention involves the identification and preparation of vascular endothelial growth factor-E (VEGF-E). VEGF-E is a novel polypeptide related to vascular endothelial growth factor (VEGF) and bone morphogenetic protein 1. VEGF-E has homology to VEGF including conservation of the amino acids required for activity of VEGF. VEGF-E can be useful in wound repair, as well as in the generation and regeneration of tissue.

7 Claims, 5 Drawing Sheets

OTHER PUBLICATIONS

Adamis et al., "Inhibition of Vascular Endothelial Growth Factor Prevents Retinal Ischemia-Associated Iris Neovascularization in a Nonhuman Primate" *Arch. Ophthalmology* 114(1):66-71 (1996).

Aiello et al., "Vascular endothelial growth factor in ocular fluid of patients with diabetic retinopathy and other retinal disorders" *New England J. of Medicine* 331(22):1480-1487 (1994).

Berkman et al., "Expression of the vascular permeability factor/ vascular endothelial growth factor gene in central nervous system neoplasms" *J. Clin. Invest.* 91(1):153-159 (1993).

Borgstrom et al., "Complete inhibition of angiogenesis and growth of microtumors by anti-vascular endothelial growth factor neutralizing antibody: novel concepts of angiostatic therapy from intravital videomicroscopy" *Cancer Research* 56(17):4032-4039 (1996).

Brown et al., "Expression of vascular permeability factor (vascular endothelial growth factor) and its receptors in adenocarcinomas of the gastrointestinal tract" *Cancer Research* 53(19):4727-4735 (1993).

Brown et al., "Expression of vascular permeability factor (vascular endothelial growth factor) and its receptors in breast cancer" *Human Pathology* 26(1):86-91 (1995).

Burgess and Maciag, "The Heparin-Binding (Fibroblast) Growth Factor Family of Proteins" *Annu. Rev. Biochem.* 58:575-606 (1989).

Clapp et al., "The 16-kilodalton N-terminal fragment of human prolactin is a potent inhibitor of angiogenesis" *Endocrinology* 133(3):1292-1299 (1993).

Connolly et al, "Human Vascular Permeability Factor" *Journal of Biological Chemistry* 264(33):20017-20024 (1989).

Dvorak et al., "Vascular permeability factor/vascular endothelial growth factor, microvascular hyperpermeability, and angiogenesis" *American Journal of Pathology* 146(5):1029-1039 (1995).

Ferrara and Davis-Smyth., "The Biology of Vascular Endothelial Growth Factor." *Endocrine Reviews.* 18(1):4-25 (1997).

Ferrara and Henzel, "Pituitary Follicular Cells Secrete a Novel Heparin-binding Growth Factor Specific for Vascular Endothelial Cells" *Biochem. & Biophys. Res. Comm.* 161(2) 851-858 (1989).

Ferrara et al., "Molecular and biological properties of the vascular endothelial growth factor family of proteins" *Endo. Rev.* 13:18-32 (1992).

Ferrara et al.. "The vascular endothelial growth factor family of polypeptides" *J. Cell. Biochem.* 47:211-218 (1991).

Folkman and Shing, "Angiogenesis" *Journal of Biological Chemistry* 267:10931-10934 (1992).

Folkman et al.. "Induction of angiogenesis during the transition from hyperplasia to neoplasia" *Nature* 339(6219):58-61 (1989).

Good et al., "A tumor suppressor-dependent inhibitor of angiogenesis is immunologically and functionally indistinguishable from a fragment of thrombospondin" *Proc. Natl. Acad. Sci. USA* 87(17):6624-6628 (1990).

Horak et al., "Angiogenesis, assessed by platelet/endothelial cell adhesion molecule antibodies, as indicator of node metastases and survival in breast cancer" *Lancet* 340(8828):1120-1124 (1992).

Houck et al., "The Vascular Endothelial Growth Factor Family: Identification of a Fourth Molecular Species and Characterization of Alternative Splicing of RNA." *Mol Endocrinol.* 5:1806-1814 (1991).

Ishikawa et al., "Identification of Angiogenic Activity and the Cloning and Expression of Platelet-Derived Endothelial Cell Growth Factor." *Nature.* 338:557-562 (1989).

Keck et al., "Vascular Permeability Factor, An Endothelial Cell Mitogen Related to PDGF" *Science* 246:1309-1312 (1989).

Kim et al., "Inhibition of Vascular Endothelial Growth Factor-Induced Angiogenesis Suppresses Tumour Growth in vivo" *Nature* 362:841-844 (1993).

Klagsbrun and D'Amore, "Regulators of angiogenesis" *Ann. Rev. Physiol.* 53:217-239 (1991).

Leung et al., "Vascular Endothelial Growth Factor is a Secreted Angiogenic Mitogen" *Science* 246:1306-1309 (1989).

Levine et al., "Bone morphogenetic protein promotes vascularization and osteoinduction in performed hydroxyapatite in the rabbit" *Annals of Plastic Surgery* 39(2):158-168 (Aug. 1997).

Lopez et al., "Transdifferentiated retinal pigment epithelial cells are immunoreative for vascular endothelial growth factor in surgically excised age-related macular degeneration-related choroidal neovascular membranes" *Invest. Ophthalmol. Vis. Sci.* 37(5):855-868 (1996).

Macchiarini et al., "Relation of neovascularisation to metastasis of non-small-cell lung cancer" *Lancet* 340(8812):145-146 (1992).

Mattern et al., "Association of vascular endothelial growth factor expression with intratumoral microvessel density and tumour cell proliferation in human epidermoid lung carcinoma" *Brit. J. Cancer* 73(7):931-934 (1996).

Melnyk et al., "Vascular endothelial growth factor promotes tumor dissemination by a mechanism distinct from its effect on primary tumor growth" *Cancer Research* 56(4):921-924 (1996).

O'Reilly et al., "Angiostatin: a novel angiogenesis inhibitor that mediates the suppression of metastases by a Lewis lung carcinoma" *Cell* 79(2):315-328 (1994).

O'Reilly et al., "Endostatin: an endogenous inhibitor of angiogenesis and tumor growth" *Cell* 88(2):277-285 (1997).

Takahara et al., "Bone morphogenetic protein-1 and a mammalian tolloid homologue (mTld) are encoded by alternatively spliced transcripts which are differentially expressed in some tissues" *Journal of Biological Chemistry* 269(51):32572-32578 (Dec. 23, 1994).

Tischer et al., "Vascular Endothelial Growth Factor: A New Member of the Platelet-Derived Growth Factor Gene Family." *Biochem. & Biophys. Res. Comm.* 165:1198-1206 (1989).

Tsai et al., "Identification of a novel platelet-derived growth factor-like gene, fallotein, in the human reproductive tract" *Biochimica et Biophysica Acta* 1492:196-202 (2000).

Warren et al., "Regulation by vascular endothelial growth factor of human colon cancer tumorigenesis in a mouse model of experimental liver metastasis" *J. Clin. Invest.* 95(4):1789-1797 (1995).

Weidner et al., "Tumor angiogenesis and metastasis—correlation in invasive breast carcinoma" *New England J. of Medicine* 324(1):1-8 (1991).

Zou et al., "Distinct roles of type I bone morphogenetic protein receptors in the formation and differentiation of cartilage" *Gene & Development* 11(17):2191-2203 (Sep. 1, 1997).

Bork, et al., "Go hunting in sequence databases but watc out for the traps" *Trends in Genetics* 12(10):425-427 (Oct. 1996).

Bork, P., "Powers and Pitfalls in Sequence Analysis: The 70% Hurdle" *Genome Research* 10(4):398-400 (Apr. 2000).

Brenner, S.E., "Errors in genome annotation" *Trends in Genetics* 15(4):132-133 (Apr. 1999).

Doerks, et al., "Protein annotation: detective work for function prediction" *Trends in Genetics* 14(6):248-250 (Jun. 1998).

Duesterhoeft et al., "Locus AL040028, Mar. 10, 1998, Accessed Feb. 26, 2000" *German Genome Project.*

Gayle et al., "Identification of regions in interleukin-1 alpha important for activity" *Journal of Biological Chemistry* 268(29):22105-22111 (Oct. 1993).

Hillier et al., "Generation and Analysis of 280,000 Human Expressed Sequence Tags" *Genome Research* 6(9):807-828 (1996).

Hollenbaugh, et al., "Recombinant globulins: novel research tools and possible pharmaceuticals" *Current Protocols in Immunology* 2:10.19.1-10.19-.11 (Apr. 1992).

Luckow et al., "Trends in the Development of Baculovirus Expression Vectors" *Bio/Technology* 6:47-55 (1988).

Marra et al., "Locus AA106035, Submitted Sep. 12, 1996, Accessed Feb. 26, 2000" *The WashU-HHMI Mouse EST project.*

National Cancer Institute Cancer Genome Anatomy Project *Locus AI1024617*, Sep. 12, 1996, Accessed Feb. 26, 2000.

National Cancer Institute Cancer Genome Anatomy Project *Locus AW05220*, Dec. 20, 1995, Accessed Feb. 26, 2000.

National Cancer Institute Cancer Genome Project *Locus AA759138*, Jan. 19, 1998, Accessed Feb. 26, 2000.

Ngo et al. *The Protein Folding Problem and Tertiary Struction Prediction*, Merz and Le Grand (Eds), Springer Verlag pp. 492-495 (Aug. 1994).

Skolnick et al., "From Genes to protein structure and function: novel applications of computational approaches in the genomic era" *Trends in Biotechnology* 18(1):34-39 (Jan. 2000).

Smith, et al., "The challenges of genome sequence annotation or "The devil is in the details"" *Nature Biotechnology* 15(12):1222-1223 (Nov. 1997).

Wells, J. A., "Additivity of Mutational Effects in Proteins" *Biochemistry* 29(37):8509-8517 (Sep. 18, 1990).

Whisstock et al., "Prediction of protein function from protein sequence and structure" *Q. Rev Biophys* 36(3):307-340 (Aug. 2003).

* cited by examiner

GACGCGTGGGCGGACGCGTGGGCTGGTTCAGGTCCAGGTTTTGCTTTGATCCTTTTCAAA
AACTGGAGACACAGAAGAGGGCTCTAGGAAAAAGTTTTGGATGGGATTATGTGGAAACTA
CCCTGCGATTCTCTGCTGCCAGAGCAGGCTCGGCGCTTCCACCCCAGTGCAGCCTTCCCC
TGGCGGTGGTGAAAGAGACTCGGGAGTCGCTGCTTCCAAAGTGCCCGCCGTGAGTGAGCT
CTCACCCCAGTCAGCCAA

ATGAGCCTCTTCGGGCTTCTCCTGCTGACATCTGCCCTGGCCGGCCAGAGACAGGGGACT
CAGGCGGAATCCAACCTGAGTAGTAAATTCCAGTTTTCCAGCAACAAGGAACAGAACGGA
GTACAAGATCCTCAGCATGAGAGAATTATTACTGTGTCTACTAATGGAAGTATTCACAGC
CCAAGGTTTCCTCATACTTATCCAAGAAATACGGTCTTGGTATGGAGATTAGTAGCAGTA
GAGGAAAATGTATGGATACAACTTACGTTTGATGAAAGATTGGGCTTGAAGACCCAGAA
GATGACATATGCAAGTATGATTTTGTAGAAGTTGAGGAACCCAGTGATGGAACTATATTA
GGGCGCTGGTGTGGTTCTGGTACTGTACCAGGAAAACAGATTTCTAAAGGAAATCAAATT
AGGATAAGATTTGTATCTGATGAATATTTTCCTTCTGAACCAGGGTTCTGCATCCACTAC
AACATTGTCATGCCACAATTCACAGAAGCTGTGAGTCCTTCAGTGCTACCCCCTTCAGCT
TTGCCACTGGACCTGCTTAATAATGCTATAACTGCCTTTAGTACCTTGGAAGACCTTATT
CGATATCTTGAACCAGAGAGATGGCAGTTGGACTTAGAAGATCTATATAGGCCAACTTGG
CAACTTCTTGGCAAGGCTTTTGTTTTGGAAGAAAATCCAGAGTGGTGGATCTGAACCTT
CTAACAGAGGAGGTAAGATTATACAGCTGCACACCTCGTAACTTCTCAGTGTCCATAAGG
GAAGAACTAAAGAGAACCGATACCATTTTCTGGCCAGGTTGTCTCCTGGTTAAACGCTGT
GGTGGGAACTGTGCCTGTTGTCTCCACAATTGCAATGAATGTCAATGTGTCCCAAGCAAA
GTTACTAAAAAATACCACGAGGTCCTTCAGTTGAGACCAAAGACCGGTGTCAGGGGATTG
CACAAATCACTCACCGACGTGGCCCTGGAGCACCATGAGGAGTGTGACTGTGTGTGCAGA
GGGAGCACAGGAGGATAGCCGCATCACCACCAGCAGCTCTTGCCCAGAGCTGTGCAGTGC
AGTGGCTGATTCTATTAGAGAACGTATGCGTTATCTCCATCCTTAATCTCAGTTGTTTGC
TTCAAGGACCTTTCATCTTCAGGATTTACAGTGCATTCTGAAAGAGGAGACATCAAACAG
AATTAGGAGTTGTGCAACAGCTCTTTTGAGAGGAGGCCTAAAGGACAGGAGAAAAGGTCT
TCAATCGTGGAAAGAAAATTAAATGTTGTATTAAATAGATCACCAGCTAGTTTCAGAGTT
ACCATGTACGTATTCCACTAGCTGGGTTCTGTATTTCAGTTCTTTCGATACGGCTTAGGG
TAATGTCAGTACAGGAAAAAAACTGTGCAAGTGAGCACCTGATTCCGTTGCCTTGCTTAA
CTCTAAAGCTCCATGTCCTGGGCCTAAAATCGTATAAAATCTGGATTTTTTTTTTTTTTT
TTGCTCATATTCACATATGTAAACCAGAACATTCTATGTACTACAAACCTGGTTTTTAAA
AAGGAACTATGTTGCTATGAATTAAACTTGTGTCATGCTGATAGGACAGACTGGATTTTT
CATATTTCTTATTAAAATTTCTGCCATTTAGAAGAAGAGAACTACATTCATGGTTTGGAA
GAGATAAACCTGAAAAGAAGAGTGGCCTTATCTTCACTTTATCGATAAGTCAGTTTATTT
GTTCATTGTGTACATTTTTATATTCTCCTTTTGACATTATAACTGTTGGCTTTTCTAAT
CTTGTTAAATATATCTATTTTTACCAAAGGTATTTAATATTCTTTTTTATGACAACTTAG
ATCAACTATTTTTAGCTTGGTAAATTTTTCTAAACACAATTGTTATAGCCAGAGGAACAA
AGATGATATAAAATATTGTTGCTCTGACAAAAATACATGTATTTCATTCTCGTATGGTGC
TAGAGTTAGATTAATCTGCATTTTAAAAAACTGAATTGGAATAGAATTGGTAAGTTGCAA
AGACTTTTTGAAAATAATTAAATTATCATATCTTCCATTCCTGTTATTGGAGATGAAAAT
AAAAAGCAACTTATGAAAGTAGACATTCAGATCCAGCCATTACTAACCTATTCCTTTTTT
GGGGAAATCTGAGCCTAGCTCAGAAAAACATAAAGCACCTTGAAAAGACTTGGCAGCTT
CCTGATAAAGCGTGCTGTGCTGTGCAGTAGGAACACATCCTATTTATTGTGATGTTGTGG
TTTTATTATCTTAAACTCTGTTCCATACACTTGTATAAATACATGGATATTTTTATGTAC
AGAAGTATGTCTCTTAACCAGTTCACTTATGTACTCTGGCAATTTAAAAGAAAATCAGT
AAAATATTTTGCTTGTAAAATGCTTAATATNGTGCCTAGGTTATGTGGTGACTATTTGAA
TCAAAAATGTATTGAATCATCAAATAAAAGAATGTGGCTATTTTGGGGAGAAAATTAAAA
AAAAAAAAAAAAAAAAAAGGTTTAGGGATAACAGGGTAATGCGGCCGC SEQ. ID NO:1

FIG. 1

MSLFGLLLLTSALAGQRQGTQAESNLSSKFQFSSNKEQNGVQDPQHERIITVSTNGSIHS
PRFPHTYPRNTVLVWRLVAVEENVWIQLTFDERFGLEDPEDDICKYDFVEVEEPSDGTIL
GRWCGSGTVPGKQISKGNQIRIRFVSDEYFPSEPGFCIHYNIVMPQFTEAVSPSVLPPSA
LPLDLLNNAITAFSTLEDLIRYLEPERWQLDLEDLYRPTWQLLGKAFVFGRKSRVVDLNL
LTEEVRLYSCTPRNFSVSIREELKRTDTIFWPGCLLVKRCGGNCACCLHNCNECQCVPSK
VTKKYHEVLQLRPKTGVRGLHKSLTDVALEHHEECDCVCRGSTGG    SEQ. ID NO:2

FIG. 2 no growth factor(s)

vegf/bfgf/pma vegf/bfgf vegf/pma

+VEGF-E-IgG @ 1% dilution

Buffer control @ 1% dilution

+VEGF-E-poly-His @ 1% dilution

Buffer control @ 1% dilution

SEQUENCE LISTING

```
<160> NUMBER OF SEQ ID NOS: 8

<210> SEQ ID NO 1
<211> LENGTH: 2825
<212> TYPE: DNA
<213> ORGANISM: Homo sapiens
<220> FEATURE:
<221> NAME/KEY: misc_feature
<222> LOCATION: (2689)..(2689)
<223> OTHER INFORMATION: Any nucleotide

<400> SEQUENCE: 1
gacgcgtggg cggacgcgtg ggctggttca ggtccaggtt ttgctttgat cctttcaaa      60 aactggagac acagaagagg gctctaggaa aaagttttgg atgggattat gtggaaacta    120
ccctgcgatt ctctgctgcc agagcaggct cggcgcttcc acccagtgc agccttcccc     180 tggcggtggt gaaagagact cgggagtcgc tgcttccaaa gtcccgccg tgagtgagct     240 ctcaccccag tcagccaaat gagcctcttc gggcttctcc tgctgacatc tgccctggcc    300
ggccagagac aggggactca ggcggaatcc aacctgagta gtaaattcca gttttccagc    360
aacaaggaac agaacggagt acaagatcct cagcatgaga gaattattac tgtgtctact    420
aatggaagta ttcacagccc aaggtttcct catacttatc caagaaatac ggtcttggta    480
tggagattag tagcagtaga ggaaaatgta tggatacaac ttacgtttga tgaaagattt    540
gggcttgaag acccagaaga tgacatatgc aagtatgatt ttgtagaagt tgaggaaccc    600
agtgatggaa ctatattagg gcgctggtgt ggttctggta ctgtaccagg aaaacagatt    660
tctaaaggaa atcaaattag gataagattt gtatctgatg aatattttcc ttctgaacca    720
gggttctgca tccactacaa cattgtcatg ccacaattca cagaagctgt gagtccttca    780
gtgctacccc cttcagcttt gccactggac ctgcttaata atgctataac tgcctttagt    840
accttggaag accttattcg atatcttgaa ccagagagat ggcagttgga cttagaagat    900
ctatataggc caacttggca acttcttggc aaggcttttg tttttggaag aaaatccaga    960
gtggtggatc tgaaccttct aacagaggag gtaagattat acagctgcac acctcgtaac   1020
ttctcagtgt ccataaggga agaactaaag agaaccgata ccattttctg gccaggttgt   1080
ctcctggtta aacgctgtgg tgggaactgt gcctgttgtc tccacaattg caatgaatgt   1140
caatgtgtcc caagcaaagt tactaaaaaa taccacgagg tccttcagtt gagaccaaag   1200
accggtgtca ggggattgca caaatcactc accgacgtgg ccctggagca ccatgaggag   1260
tgtgactgtg tgtgcagagg gagcacagga ggatagccgc atcaccacca gcagctcttg   1320
cccagagctg tgcagtgcag tggctgattc tattagagaa cgtatgcgtt atctccatcc   1380
```

```
ttaatctcag ttgtttgctt caaggacctt tcatcttcag gatttacagt gcattctgaa      1440
agaggagaca tcaaacagaa ttaggagttg tgcaacagct cttttgagag gaggcctaaa      1500
ggacaggaga aaaggtcttc aatcgtggaa agaaaattaa atgttgtatt aaatagatca      1560
ccagctagtt tcagagttac catgtacgta ttccactagc tgggttctgt atttcagttc      1620
tttcgatacg gcttagggta atgtcagtac aggaaaaaaa ctgtgcaagt gagcacctga      1680
ttccgttgcc ttgcttaact ctaaagctcc atgtcctggg cctaaaatcg tataaaatct      1740 ggatttttt ttttttttt gctcatattc acatatgtaa accagaacat tctatgtact       1800
acaaacctgg tttttaaaaa ggaactatgt tgctatgaat taaacttgtg tcatgctgat      1860
aggacagact ggattttca tatttcttat taaaatttct gccatttaga agaagagaac       1920
tacattcatg gtttggaaga gataaacctg aaaagaagag tggccttatc ttcactttat      1980
cgataagtca gttatttgt ttcattgtgt acatttttat attctccttt tgacattata       2040
actgttggct tttctaatct tgttaaatat atctattttt accaaggta tttaatattc       2100 tttttatga caacttagat caactatttt tagcttggta aattttcta acacaattg         2160 ttatagccag aggaacaaag atgatataaa atattgttgc tctgacaaaa atacatgtat      2220
ttcattctcg tatggtgcta gagttagatt aatctgcatt ttaaaaaact gaattggaat      2280
agaattggta agttgcaaag acttttgaa ataattaaa ttatcatatc ttccattcct        2340
gttattggag atgaaaataa aaagcaactt atgaaagtag acattcagat ccagccatta      2400
ctaacctatt cctttttgg ggaaatctga gcctagctca gaaaaacata aagcaccttg       2460
aaaaagactt ggcagcttcc tgataaagcg tgctgtgctg tgcagtagga acacatccta      2520
tttattgtga tgttgtggtt ttattatctt aaactctgtt ccatacactt gtataaatac      2580
atggatattt ttatgtacag aagtatgtct cttaaccagt tcacttattg tactctggca      2640
atttaaaaga aaatcagtaa aatattttgc ttgtaaaatg cttaatatng tgcctaggtt      2700
atgtggtgac tatttgaatc aaaaatgtat tgaatcatca aataaagaa tgtggctatt       2760 ttggggagaa aattaaaaaa aaaaaaaaaa aaaaaggttt agggataaca gggtaatgcg      2820
gccgc                                                                 2825
```

<210> SEQ ID NO 2
<211> LENGTH: 345
<212> TYPE: PRT
<213> ORGANISM: Homo sapiens

<400> SEQUENCE: 2

```
Met Ser Leu Phe Gly Leu Leu Leu Thr Ser Ala Leu Ala Gly Gln
1               5                   10                  15

Arg Gln Gly Thr Gln Ala Glu Ser Asn Leu Ser Ser Lys Phe Gln Phe
                20                  25                  30

Ser Ser Asn Lys Glu Gln Asn Gly Val Gln Asp Pro Gln His Glu Arg
            35                  40                  45

Ile Ile Thr Val Ser Thr Asn Gly Ser Ile His Ser Pro Arg Phe Pro
        50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
                100                 105                 110
```

```
Glu Pro Ser Asp Gly Thr Ile Leu Gly Arg Trp Cys Gly Ser Gly Thr
            115                 120                 125

Val Pro Gly Lys Gln Ile Ser Lys Gly Asn Gln Ile Arg Ile Arg Phe
    130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
            180                 185                 190

Phe Ser Thr Leu Glu Asp Leu Ile Arg Tyr Leu Glu Pro Glu Arg Trp
            195                 200                 205

Gln Leu Asp Leu Glu Asp Leu Tyr Arg Pro Thr Trp Gln Leu Leu Gly
    210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Leu Val Lys Arg Cys Gly Asn Cys Ala Cys Cys Leu
            275                 280                 285

His Asn Cys Asn Glu Cys Gln Cys Val Pro Ser Lys Val Thr Lys Lys
    290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His Glu Glu Cys Asp
                325                 330                 335

Cys Val Cys Arg Gly Ser Thr Gly Gly
            340                 345

<210> SEQ ID NO 3
<211> LENGTH: 21
<212> TYPE: DNA
<213> ORGANISM: Artificial Sequence
<220> FEATURE:
<223> OTHER INFORMATION: Sequence is synthesized

<400> SEQUENCE: 3
acttctcagt gtccataagg g                                          21

<210> SEQ ID NO 4
<211> LENGTH: 40
<212> TYPE: DNA
<213> ORGANISM: Artificial Sequence
<220> FEATURE:
<223> OTHER INFORMATION: Sequence is synthesized

<400> SEQUENCE: 4
gaactaaaga gaaccgatac cattttctgg ccaggttgtc                      40

<210> SEQ ID NO 5
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 5
```

```
caccacagcg tttaaccagg                                              20

<210> SEQ ID NO 6
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 6
acaacaggca cagttcccac                                              20

<210> SEQ ID NO 7
<211> LENGTH: 48
<212> TYPE: DNA
<213> ORGANISM: Artificial Sequence
<220> FEATURE:
<223> OTHER INFORMATION: Sequence is synthesized

<400> SEQUENCE: 7
ggattctaat acgactcact atagggcggc ggaatccaac ctgagtag               48

<210> SEQ ID NO 8
<211> LENGTH: 47
<212> TYPE: DNA
<213> ORGANISM: Artificial Sequence
<220> FEATURE:
<223> OTHER INFORMATION: Sequence is synthesized

<400> SEQUENCE: 8
ctatgaaatt aaccctcact aaagggagcg gctatcctcc tgtgctc                47
```

ANTIBODIES TO POLYPEPTIDES HOMOLOGOUS TO VEGF AND BMP1

RELATED APPLICATIONS

This application is a divisional of U.S. application Ser. No. 09/265,686 filed Mar. 10, 1999, now U.S. Pat. No. 6,455,283, which is a continuation-in-part of U.S. application Ser. No. 09/184,216 filed Nov. 2, 1998, now abandoned, which is a continuation-in-part of U.S. application Ser. No. 09/040,220 filed Mar. 17, 1998, now U.S. Pat. No. 6,391,311, the disclosures of which are incorporated herein by reference.

FIELD OF THE INVENTION

The present invention is directed to polypeptides related to vascular endothelial cell growth factor (hereinafter sometimes referred to as VEGF) and bone morphogenetic protein 1 (hereinafter sometimes referred to as BMP1), termed herein as VEGF-E polypeptides, nucleic acids encoding therefor, methods for preparing VEGF-E, and methods, compositions, and assays utilizing VEGF-E.

BACKGROUND OF THE INVENTION

Various naturally occurring polypeptides reportedly induce the proliferation of endothelial cells. Among those polypeptides are the basic and acidic fibroblast growth factors (FGF) (Burgess and Maciag, *Annual Rev. Biochem.*, 58: 575 (1989)), platelet-derived endothelial cell growth factor (PD-ECGF) (Ishikawa et al., *Nature*, 338: 557 (1989)), and vascular endothelial growth factor (VEGF). Leung et al., *Science*, 246: 1306 (1989); Ferrara and Henzel, *Biochem. Biophys. Res. Commun.*, 161: 851 (1989); Tischer et al., *Biochem. Biophys. Res. Commun.*, 165: 1198 (1989); EP 471,754B granted Jul. 31, 1996.

The heparin-binding endothelial cell-growth factor, VEGF, was identified and purified from media conditioned by bovine pituitary follicular or folliculo-stellate cells several years ago. See Ferrara et al., *Biophys. Res. Comm.*, 161: 851 (1989). Media conditioned by cells transfected with the human VEGF (hVEGF) cDNA promoted the proliferation of capillary endothelial cells, whereas control cells did not. Leung et al., *Science*, 246: 1306 (1989). VEGF is a naturally occurring compound that is produced in follicular or folliculo-stellate cells (FC), a morphologically well-characterized population of granular cells. The FC are stellate cells that send cytoplasmic processes between secretory cells.

VEGF is expressed in a variety of tissues as multiple homodimeric isoforms (121, 165, 189 and 206 amino acids per monomer), also collectively referred to as hVEGF-related proteins, resulting from alternative RNA splicing. The 121-amino acid protein differs from hVEGF by virtue of the deletion of the 44 amino acids between residues 116 and 159 in hVEGF. The 189-amino acid protein differs from hVEGF by virtue of the insertion of 24 amino acids at residue 116 in hVEGF, and apparently is identical to human vascular permeability factor (hVPF). The 206-amino acid protein differs from hVEGF by virtue of an insertion of 41 amino acids α-residue 116 in hVEGF. Houck et al., *Mol. Endocrin.*, 5: 1806 (1991); Ferrara et al., *J. Cell. Biochem.*, 47: 211 (1991); Ferrara et al., *Endocrine Reviews*, 13: 18 (1992); Keck et al., *Science*, 246: 1309 (1989); Connolly et al., *J. Biol. Chem.*, 264: 20017 (1989); EP 370,989 published May 30, 1990. $VEGF_{121}$ is a soluble mitogen that does not bind heparin; the longer forms of VEGF bind heparin with progressively higher affinity. The heparin-binding forms of VEGF can be cleaved in the carboxy terminus by plasmin to release (a) diffusible form(s) of VEGF. The amino acid sequence of the carboxy-terminal peptide identified after plasmin cleavage is $Arg_{110}$-$Ala_{111}$. Amino terminal "core" protein, VEGF (1-110), isolated as a homodimer, binds neutralizing monoclonal antibodies (4.6.1 and 2E3) and soluble forms of FMS-like tyrosine kinase (FLT-1), kinase domain region (KDR) and fetal liver kinase (FLK) receptors with similar affinity compared to the intact $VEGF_{165}$ homodimer.

As noted, VEGF contains two domains that are responsible respectively for binding to the KDR and FLT-1 receptors. These receptors exist only on endothelial (vascular) cells. As cells become depleted in oxygen, because of trauma and the like, VEGF production increases in such cells which then bind to the respective receptors in order to signal ultimate biological effect. The signal then increases vascular permeability and the cells divide and expand to form new vascular pathways—vasculogenesis and angiogenesis.

Thus, VEGF is useful for treating conditions in which a selected action on the vascular endothelial cells, in the absence of excessive tissue growth, is important, for example, diabetic ulcers and vascular injuries resulting from trauma such as subcutaneous wounds. Being a vascular (artery and venus) endothelial cell growth factor, VEGF restores cells that are damaged, a process referred to as vasculogenesis, and stimulates the formulation of new vessels, a process referred to as angiogenesis.

VEGF would also find use in the restoration of vasculature after a myocardial infarct, as well as other uses that can be deduced. In this regard, inhibitors of VEGF are sometimes desirable, particularly to mitigate processes such as angiogenesis and vasculogenesis in cancerous cells.

It is now well established that angiogenesis, which involves the formation of new blood vessels from preexisting endothelium, is implicated in the pathogenesis of a variety of disorders. These include solid tumors and metastasis, atherosclerosis, retrolental fibroplasia, hemangiomas, chronic inflammation, intraocular neovascular syndromes such as proliferative retinopathies, e.g., diabetic retinopathy, age-related macular degeneration (AMD), neovascular glaucoma, immune rejection of transplanted corneal tissue and other tissues, rheumatoid arthritis, and psoriasis. Folkman et al., *J. Biol. Chem.*, 267: 10931-10934 (1992); Klagsbrun et al., *Annu. Rev. Physiol.*, 53: 217-239 (1991); and Garner A, "Vascular diseases", In: *Pathobiology of Ocular Disease. A Dynamic Approach*, Garner A, Klintworth GK, Eds., 2nd Edition (Marcel Dekker, NY, 1994), pp 1625-1710.

In the case of tumor growth, angiogenesis appears to be crucial for the transition from hyperplasia to neoplasia, and for providing nourishment to the growing solid tumor. Folkman et al., *Nature*, 339: 58 (1989). The neovascularization allows the tumor cells to acquire a growth advantage and proliferative autonomy compared to the normal cells. Accordingly, a correlation has been observed between density of microvessels in tumor sections and patient survival in breast cancer as well as in several other tumors. Weidner et al., *N Engl J Med*, 324: 1-6 (1991); Horak et al., *Lancet*, 340: 1120-1124 (1992); Macchiarini et al., *Lancet*, 340: 145-146 (1992).

The search for positive regulators of angiogenesis has yielded many candidates, including aFGF, bFGF, TGF-α, TGF-β, HGF, TNF-α, angiogenin, IL-8, etc. Folkman et al., *J.B.C.*, supra, and Klagsbrun et al., supra. The negative regulators so far identified include thrombospondin (Good et al., *Proc. Natl. Acad. Sci. USA.*, 87: 6624-6628 (1990)), the 16-kilodalton N-terminal fragment of prolactin (Clapp et al., *Endocrinology*, 133: 1292-1299 (1993)), angiostatin (O[]Reilly et al. *Cell*, 79: 315-328 (1994)), and endostatin. O[]Reilly et al., *Cell*, 88: 277-285 (1996). Work done over the last several years has established the key role of VEGF, not only in stimulating vascular endothelial cell proliferation, but also in inducing vascular permeability and angiogenesis. Ferrara et al., *Endocr. Rev.*, 18: 4-25 (1997). The finding that the loss of even a single VEGF allele results in embryonic lethality points to an irreplaceable role played by this factor in the development and differentiation of the vascular system. Furthermore, VEGF has been shown to be a key mediator of neovascularization associated with tumors and intraocular disorders. Ferrara et al., *Endocr. Rev.*, supra. The VEGF mRNA is overexpressed by the majority of human tumors examined. Berkman et al., *J Clin Invest*, 91: 153-159 (1993); Brown et al., *Human Pathol.*, 26: 86-91 (1995); Brown et al., *Cancer Res.*, 53: 4727-4735 (1993); Mattern et al., *Brit. J. Cancer*, 73: 931-934 (1996); Dvorak et al., *Am J. Pathol.*, 146: 1029-1039 (1995).

Also, the concentration levels of VEGF in eye fluids are highly correlated to the presence of active proliferation of blood vessels in patients with diabetic and other ischemia-related retinopathies. Aiello et al., *N. Engl. J. Med.*, 331: 1480-1487 (1994). Furthermore, recent studies have demonstrated the localization of VEGF in choroidal neovascular membranes in patients affected by AMD. Lopez et al., *Invest. Ophthalmol. Vis. Sci.*, 37: 855-868 (1996). Anti-VEGF neutralizing antibodies suppress the growth of a variety of human tumor cell lines in nude mice (Kim et al., *Nature*, 362: 841-844 (1993); Warren et al., *J. Clin. Invest.*, 95: 1789-1797 (1995); Borgström et al., *Cancer Res.*, 56: 4032-4039 (1996); Melnyk et al., *Cancer Res.*, 56: 921-924 (1996)) and also inhibit intraocular angiogenesis in models of ischemic retinal disorders. Adamis et al., *Arch. Ophthalmol.*, 114: 66-71 (1996). Therefore, anti-VEGF monoclonal antibodies or other inhibitors of VEGF action are promising candidates for the treatment of solid tumors and various intraocular neovascular disorders. Such antibodies are described, for example, in EP 817,648 published Jan. 14, 1998 and in PCT/US 98/06724 filed Apr. 3, 1998.

Regarding the bone morphogenetic protein family, members of this family have been reported as being involved in the differentiation of cartilage and the promotion of vascularization and osteoinduction in preformed hydroxyapatite. Zou, et al., *Genes Dev.* (U.S.), 11(17):2191 (1997); Levine, et al., *Ann. Plast. Surg.*, 39(2):158 (1997). A number of related bone morphogenetic proteins have been identified, all members of the bone morphogenetic protein (BMP) family. Bone morphogenetic native and mutant proteins, nucleic acids encoding them, related compounds including receptors, host cells, and uses are further described in at least: U.S. Pat. Nos. 5,670,338; 5,454,419; 5,661,007; 5,637,480; 5,631,142; 5,166,058; 5,620,867; 5,543,394; 4,877,864; 5,013,649; 5,106,748; and 5,399,677. Of particular interest are proteins having homology with bone morphogenetic protein 1, a procollagen C-proteinase that plays key roles in regulating matrix deposition.

In view of the role of vascular endothelial cell growth and angiogenesis in many diseases and disorders, it is desirable to have a means of reducing or inhibiting one or more of the biological effects causing these processes. It is also desirable to have a means of assaying for the presence of pathogenic polypeptides in normal and diseased conditions, and especially cancer. Further, in a specific aspect, as there is no generally applicable therapy for the treatment of cardiac hypertrophy, the identification of factors that can prevent or reduce cardiac myocyte hypertrophy is of primary importance in the development of new therapeutic strategies to inhibit pathophysiological cardiac growth. While there are several treatment modalities for various cardiovascular and oncologic disorders, there is still a need for additional therapeutic approaches.

The present invention is predicated upon research intended to identify novel polypeptides which are related to VEGF and the BMP family, and in particular, polypeptides which have a role in the survival, proliferation, and/or differentiation of cells. While the novel polypeptides are not expected to have biological activity identical to the known polypeptides to which they have homology, the known polypeptide biological activities can be used to determine the relative biological activities of the novel polypeptides. In particular, the novel polypeptides described herein can be used in assays which are intended to determine the ability of a polypeptide to induce survival, proliferation, or differentiation of cells. In turn, the results of these assays can be used accordingly, for diagnostic and therapeutic purposes. The results of such research are the subject of the present invention.

SUMMARY OF THE INVENTION

Accordingly, in one aspect of the invention is provided isolated nucleic acid comprising a nucleotide sequence encoding a vascular endothelial cell growth factor-E (VEGF-E) polypeptide comprising amino acid residues 1 through 345 of FIG. 2 (SEQ ID NO:2). In preferred embodiments, this nucleic acid comprises the coding nucleotide sequence of FIG. 1 (i.e., it comprises residues 259 through 1293 of SEQ ID NO: 1), or its complement. In other aspects, the invention provides a vector comprising this nucleic acid, preferably one that is operably linked to control sequences recognized by a host cell transformed with the vector, as well as a host cell comprising the nucleic acid, preferably a host cell transformed with the vector. Preferably, this host cell is a Chinese Hamster Ovary cell, an insect cell, an *E. coli* cell, or a yeast cell, and is most preferably a baculovirus-infected insect cell.

In another embodiment, this invention provides a process for producing a VEGF-E polypeptide comprising culturing the host cell described above under conditions suitable for expression of the VEGF-E polypeptide and recovering the VEGF-E polypeptide from the cell culture. Further provided is a polypeptide produced by this process.

In another embodiment, the invention provides a polypeptide comprising the amino acid sequence set forth in SEQ ID NO:2.

In a further embodiment, the invention provides a chimeric polypeptide comprising the VEGF-E polypeptide fused to a heterologous amino acid sequence.

In preferred embodiments, the heterologous amino acid sequence is an epitope tag sequence or a Fc region of an immunoglobulin.

In another aspect of the invention is provided a composition comprising the VEGF-E polypeptide in admixture with a carrier. In a preferred aspect, the composition comprises a therapeutically effective amount of the polypeptide, wherein the carrier is a pharmaceutically acceptable carrier. Also preferred is where the composition further comprises a cardiovascular, endothelial, or angiogenic agent.

In a still further embodiment, the invention provides a method for preparing the composition for the treatment of a cardiovascular or endothelial disorder comprising admixing a therapeutically effective amount of the VEGF-E polypeptide with the carrier.

In another embodiment, the invention provides a pharmaceutical product comprising:

(a) the composition described above;

(b) a container containing said composition; and (c) a label affixed to said container, or a package insert included in said pharmaceutical product referring to the use of said VEGF-E polypeptide in the treatment of a cardiovascular or endothelial disorder.

In yet another embodiment, the invention provides a method for diagnosing a disease or a susceptibility to a disease related to a mutation in a nucleic acid sequence encoding VEGF-E comprising:

(a) isolating a nucleic acid sequence encoding VEGF-E from a sample derived from a host; and (b) determining a mutation in the nucleic acid sequence encoding VEGF-E.

In a still further embodiment, the invention provides a method of diagnosing cardiovascular and endothelial disorders in a mammal comprising detecting the level of expression of a gene encoding a VEGF-E polypeptide (a) in a test sample of tissue cells obtained from the mammal, and (b) in a control sample of known normal tissue cells of the same cell type, wherein a higher or lower expression level in the test sample indicates the presence of a cardiovascular or endothelial dysfunction in the mammal from which the test tissue cells were obtained.

In a further embodiment, the invention provides a method for treating a cardiovascular or endothelial disorder in a mammal comprising administering to the mammal an effective amount of a VEGF-E polypeptide. Preferably, the disorder is cardiac hypertrophy, trauma, or a bone-related disorder. Also, preferably said mammal is human. In another preferred embodiment, the disorder is cardiac hypertrophy and it is characterized by the presence of an elevated level of $PGF_{2\alpha}$, or it has been induced by myocardial infarction, where preferably said VEGF-E polypeptide administration is initiated within 48 hours following myocardial infarction. In another preferred embodiment, the cardiovascular or endothelial disorder is cardiac hypertrophy and said VEGF-E polypeptide is administered together with a cardiovascular or endothelial agent. More preferably, said cardiovascular, endothelial, or angiogenic agent is selected from the group consisting of an antihypertensive drug, an ACE-inhibitor, an endothelin receptor antagonist, and a thrombolytic agent.

In another embodiment, the invention provides a method for identifying an agonist to a VEGF-E polypeptide comprising:

(a) contacting cells and a candidate compound under conditions that allow the polypeptide to stimulate proliferation of the cells; and (b) measuring the extent to which cell proliferation is inhibited by the compound.

Further provided is an agonist to a VEGF-E polypeptide identified by the above method.

Also provided is a method for identifying a compound that inhibits the expression or activity of a VEGF-E polypeptide, comprising:

(a) contacting a candidate compound with the polypeptide under conditions and for a time sufficient to allow the compound and polypeptide to interact; and (b) measuring the extent to which the compound interacts with the polypeptide.

In another embodiment, the invention provides a compound identified by the above method.

In a still further embodiment, the invention provides a compound that inhibits the expression or activity of a VEGF-E polypeptide.

In another embodiment, the invention provides a method for treating an angiogenic disorder in a mammal comprising administering to the mammal an effective amount of an antagonist to a VEGF-E polypeptide. In a preferred embodiment, the angiogenic disorder is cancer or age-related macular degeneration. In another preferred embodiment, the mammal is human. In a further preferred aspect, an effective amount of an angiostatic agent is administered in conjunction with the antagonist. In other aspects, the invention provides an isolated antibody that binds a VEGF-E polypeptide. Preferably, this antibody is a monoclonal antibody.

In a further aspect, the invention provides a method for inhibiting angiogenesis induced by VEGF-E polypeptide in a mammal comprising administering a therapeutically effective amount of the antibody to the mammal, where preferably the mammal is a human. Also, the mammal preferably has a tumor or a retinal disorder. In another preferred aspect, the mammal has cancer and the antibody is administered in combination with a chemotherapeutic agent, a growth inhibitory agent, or a cytotoxic agent.

In another preferred embodiment, the invention provides a method for determining the presence of a VEGF-E polypeptide comprising exposing a cell suspected of containing the VEGF-E polypeptide to the antibody and determining binding of said antibody to said cell.

In yet another preferred aspect, the invention supplies a method of diagnosing cardiovascular, endothelial, or angiogenic disorders in a mammal comprising (a) contacting the antibody with a test sample of tissue cells obtained from the mammal, and (b) detecting the formation of a complex between the anti-VEGF-E antibody and the VEGF-E polypeptide in the test sample.

In still further aspects, the invention provides a cancer diagnostic kit comprising the antibody and a carrier in suitable packaging. Preferably, the kit further comprises instructions for using said antibody to detect the VEGF-E polypeptide.

In yet another embodiment, the invention provides an article of manufacture, comprising:

a container;

a label on the container; and a composition comprising an anti-VEGF-E antibody contained within the container; wherein the label on the container indicates that the composition can be used in therapeutic or diagnostic methods.

BRIEF DESCRIPTION OF THE DRAWINGS

FIG. 1 depicts a full-length DNA sequence of VEGF-E (SEQ ID NO:1), the coding region of which is from nucleotide residues 259 through 1293. SEQ ID NO:1 represents DNA:29101 deposited as DNA29101-1276 Mar. 5, 1998 at the American Type Culture Collection, Manassas, Va. It is DNA:29101, also termed UNQ:174 herein that contains the region encoding VEGF-E. The start and stop codon are circled, showing the coding region beginning with ATG and the stop codon immediately after the last coding nucleotide. The coding region, 1035 nucleic acids in length, is within SEQ ID NO:1, at positions 259 through 1293. SEQ ID NO:1 includes the nucleic acid encoding the presumed leader signal sequence or pre-protein, and the putative mature protein.

FIG. 2 depicts the deduced amino acid sequence for VEGF-E, also herein termed PRO:200, SEQ ID NO:2. This sequence represents the protein encoded by the open reading frame of UNQ:174. The corresponding molecular weight is 39,029 D. The pI is 6.06. The NX(S/T) is 3. Potential N-glycosylation sites are at positions 25, 54, and 254. CUB domains are at positions 52-65, 118-125 and 260-273.

FIG. 3B shows VEGF, bFGF and PMA combined, FIG. 3C shows VEGF and bFGF combined, FIG. 3D shows VEGF and PMA combined, FIG. 3E shows bFGF and PMA combined, FIG. 3F shows VEGF alone, FIG. 3G shows bFGF alone, and FIG. 3H shows PMA alone.

DETAILED DESCRIPTION OF THE INVENTION

I. Definitions

Figure 3A:
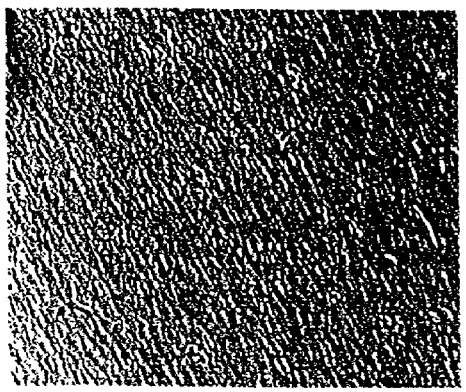
FIGS. 3A-3H show the effect of no growth factor (FIG. 3A), and one or more growth factors (VEGF, bFGF, and/or PMA) (FIGS. 3B-3H) on HUVEC tube formation.
Figure 3B:
Figure 3C:
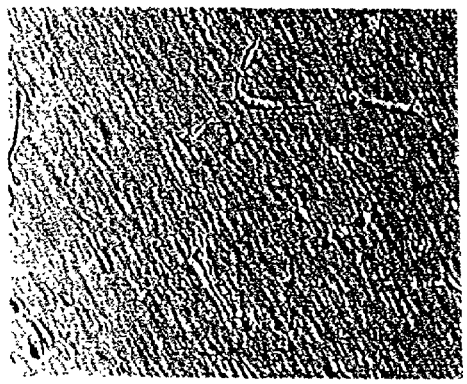
Figure 3D:
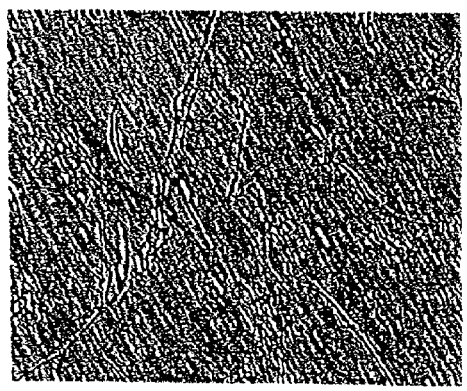
Figure 3E:
Figure 3F:
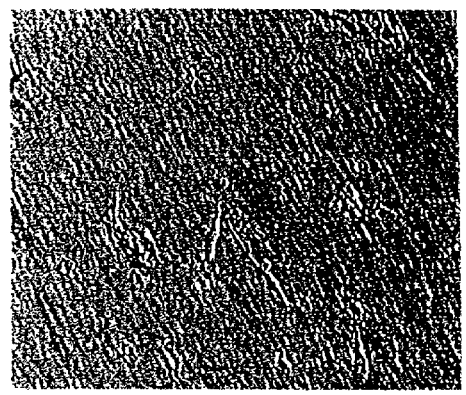
Figure 3G:
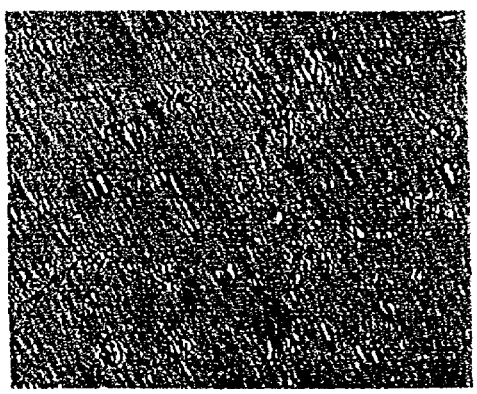
Figure 3H:
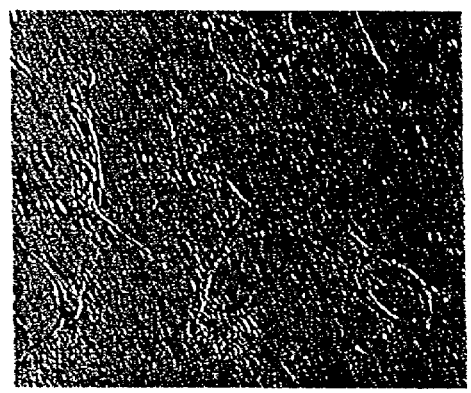

As used herein, "vascular endothelial cell growth factor-E," or "VEGF-E," refers to a mammalian growth factor as described herein, including the human amino acid sequence of FIG. 2, a sequence which has homology to VEGF and bone morphogenetic protein 1 and which includes complete conservation of all VEGF cysteine residues, which have been shown to be required for biological activity of VEGF. VEGF-E expression includes expression in human fetal bone, thymus, and the gastrointestinal tract, as well as in fetal testis, lung, and lymph nodes, and in other tissues as shown in the examples below. The biological activity of native VEGF-E is shared by any analogue or variant thereof that promotes selective growth and/or survival of umbilical vein endothelial cells, induces proliferation of pluripotent fibroblast cells, induces immediate early gene c-fos in human endothelial cell lines, causes myocyte hypertrophy in cardiac cells, inhibits VEGF-stimulated proliferation of adrenal cortical capillary endothelial cells, or which possesses an immune epitope that is immunologically cross-reactive with an antibody raised against at least one epitope of the corresponding native VEGF-E. The human VEGF-E herein is active on rat and mouse cells, indicating conservation across species. Moreover, the VEGF-E herein is expressed at the growth plate region and has been shown to embrace fetal myocytes.

As used herein, "vascular endothelial cell growth factor," or "VEGF," refers to a mammalian growth factor as defined in U.S. Pat. No. 5,332,671. The biological activity of native VEGF is shared by any analogue or variant thereof that promotes selective growth of vascular endothelial cells but not of bovine corneal endothelial cells, lens epithelial cells, adrenal cortex cells, BHK-21 fibroblasts, or keratinocytes, or that possesses an immune epitope that is immunologically cross-reactive with an antibody raised against at least one epitope of the corresponding native VEGF.

The terms "VEGF-E polypeptide" and "VEGF-E" when used herein encompass native-sequence VEGF-E polypeptide and VEGF-E polypeptide variants (which are further defined herein). The VEGF-E polypeptides may be isolated from a variety of sources, such as from human tissue types or from another source, or prepared by recombinant or synthetic methods.

A "native-sequence VEGF-E polypeptide" comprises a polypeptide having the same amino acid sequence as a VEGF-E polypeptide derived from nature. Such native-sequence VEGF-E polypeptide can be isolated from nature or can be produced by recombinant or synthetic means. The term "native-sequence VEGF-E polypeptide" specifically encompasses naturally-occurring truncated or secreted forms of a VEGF-E polypeptide, naturally-occurring variant forms (e.g., alternatively-spliced forms) and naturally-occurring allelic variants of a VEGF-E polypeptide. In one embodiment of the invention, the native-sequence VEGF-E polypeptide is a mature or full-length native sequence VEGF-E polypeptide comprising amino acids 1 through 345 as depicted in FIG. 2.

"VEGF-E variant" means an active VEGF-E polypeptide as defined below having at least about 80% amino acid sequence identity with the VEGF-E polypeptide having the deduced amino acid sequence shown in FIG. 2 for a full-length native-sequence VEGF-E polypeptide. Such VEGF-E polypeptide variants include, for instance, VEGF-E polypeptides wherein one or more amino acid residues are added, deleted, or substituted at the N- or C-terminus of the sequence of FIG. 2 or within the sequence as well as active fragments thereof. Ordinarily, a VEGF-E polypeptide variant will have at least about 80% amino acid sequence identity, more preferably at least about 90% amino acid sequence identity, and even more preferably at least about 95% amino acid sequence identity with the amino acid sequence of FIG. 2.

"Percent (%) amino acid sequence identity" with respect to the VEGF-E amino acid sequences identified herein is defined as the percentage of amino acid residues in a candidate sequence that are identical with the amino acid residues in a VEGF-E polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as ALIGN or Megalign (DNASTAR) software. Those skilled in the art can determine appropriate parameters for measuring alignment, including any algorithms needed to achieve maximal alignment over the full length of the sequences being compared.

"Percent (%) nucleic acid sequence identity" is defined as the percentage of nucleotides in a candidate sequence that are identical with the sequence shown in FIG. 1 (SEQ ID NO:1), respectively, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as ALIGN or Megalign (DNASTAR) software. Those skilled in the art can determine appropriate parameters for measuring alignment, including any algorithms needed to achieve maximal alignment over the full length of the sequences being compared.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the VEGF-E polypeptide natural environment will not be present. Ordinarily, however, isolated polypeptide will be prepared by at least one purification step.

An "isolated" VEGF-E polypeptide-encoding nucleic acid molecule is a nucleic acid molecule that is identified and separated from at least one contaminant nucleic acid molecule with which it is ordinarily associated in the natural source of the VEGF-E polypeptide-encoding nucleic acid. An isolated VEGF-E polypeptide-encoding nucleic acid molecule is other than in the former setting in which it is found in nature. Isolated VEGF-E polypeptide-encoding nucleic acid molecules therefore are distinguished from the VEGF-E polypeptide-encoding nucleic acid molecule as it exists in natural cells. However, an isolated VEGF-E polypeptide-encoding nucleic acid molecule includes VEGF-E polypeptide-encoding nucleic acid molecules contained in cells that ordinarily express VEGF-E polypeptide where, for example, the nucleic acid molecule is in a chromosomal location different from that of natural cells.

The phrases "cardiovascular and endothelial disorder" and "cardiovascular and endothelial dysfunction" are used interchangeably and refer to disorders, typically systemic, that stimulate angiogenesis and/or cardiovascularization. This includes diseases that affect vessels, as well as diseases of the vessels themselves, such as of the arteries, capillaries, veins, and/or lymphatics. Such disorders include, for example, arterial disease, such as atherosclerosis, hypertension, inflammatory vasculitides, Reynaud's disease and Reynaud's phenomenon, aneurysms, and arterial restenosis; venous and lymphatic disorders such as thrombophlebitis, lymphangitis, and lymphedema; and other vascular disorders such as peripheral vascular disease, trauma such as wounds, burns, and other injured tissue, implant fixation, scarring, ischemia reperfusion injury, rheumatoid arthritis, cerebrovascular disease, renal diseases such as acute renal failure, and osteoporosis. This would also include angina, myocardial infarctions such as acute myocardial infarctions, cardiac hypertrophy, and heart failure such as congestive heart failure (CHF).

The phrase []angiogenic disorder[] refers to a disorder that requires treatment with an agent that inhibits angiogenesis, e.g., an angiostatic compound. Such disorders include, for example, types of cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma, and tumor angiogenesis.

[]Hypertrophy[], as used herein, is defined as an increase in mass of an organ or structure independent of natural growth that does not involve tumor formation. Hypertrophy of an organ or tissue is due either to an increase in the mass of the individual cells (true hypertrophy), or to an increase in the number of cells making up the tissue (hyperplasia), or both. Certain organs, such as the heart, lose the ability to divide shortly after birth. Accordingly, []cardiac hypertrophy[]is defined as an increase in mass of the heart, which, in adults, is characterized by an increase in myocyte cell size and contractile protein content without concomitant cell division. The character of the stress responsible for inciting the hypertrophy, (e.g., increased preload, increased afterload, loss of myocytes, as in myocardial infarction, or primary depression of contractility), appears to play a critical role in determining the nature of the response. The early stage of cardiac hypertrophy is usually characterized morphologically by increases in the size of microfibrils and mitochondria, as well as by enlargement of mitochondria and nuclei. At this stage, while muscle cells are larger than normal, cellular organization is largely preserved. At a more advanced stage of cardiac hypertrophy, there are preferential increases in the size or number of specific organelles, such as mitochondria, and new contractile elements are added in localized areas of the cells, in an irregular manner. Cells subjected to long-standing hypertrophy show more obvious disruptions in cellular organization, including markedly enlarged nuclei with highly lobulated membranes, which displace adjacent myofibrils and cause breakdown of normal Z-band registration. The phrase []cardiac hypertrophy[] is used to include all stages of the progression of this condition, characterized by various degrees of structural damage of the heart muscle, regardless of the underlying cardiac disorder. Hence, the term also includes physiological conditions instrumental in the development of cardiac hypertrophy, such as elevated blood pressure, aortic stenosis, or myocardial infarction.

[]Heart failure[] refers to an abnormality of cardiac function where the heart does not pump blood at the rate needed for the requirements of metabolizing tissues. The heart failure can be caused by a number of factors, including ischemic, congenital, rheumatic, or idiopathic forms.

[]Congestive heart failure[] or []CHF[] is a progressive pathologic state where the heart is increasingly unable to supply adequate cardiac output (the volume of blood pumped by the heart over time) to deliver the oxygenated blood to peripheral tissues. As CHF progresses, structural and hemodynamic damages occur. While these damages have a variety of manifestations, one characteristic symptom is ventricular hypertrophy. CHF is a common end result of a number of various cardiac disorders.

[]Myocardial infarction[] generally results from atherosclerosis of the coronary arteries, often with superimposed coronary thrombosis. It may be divided into two major types: transmural infarcts, in which myocardial necrosis involves the full thickness of the ventricular wall, and subendocardial (nontransmural) infarcts, in which the necrosis involves the subendocardium, the intramural myocardium, or both, without extending all the way through the ventricular wall to the epicardium. Myocardial infarction is known to cause both a change in hemodynamic effects and an alteration in structure in the damaged and healthy zones of the heart. Thus, for example, myocardial infarction reduces the maximum cardiac output and the stroke volume of the heart. Also associated with myocardial infarction is a stimulation of the DNA synthesis occurring in the interstice as well as an increase in the formation of collagen in the areas of the heart not affected.

As a result of the increased stress or strain placed on the heart in prolonged hypertension due, for example, to the increased total peripheral resistance, cardiac hypertrophy has long been associated with []hypertension[]. A characteristic of the ventricle that becomes hypertrophic as a result of chronic pressure overload is an impaired diastolic performance. Fouad et al., *J. Am. Coll. Cardiol.*, 4: 1500-1506 (1984); Smith et al., *J. Am. Coll. Cardiol.*, 5: 869-874 (1985). A prolonged left ventricular relaxation has been detected in early essential hypertension, in spite of normal or supranormal systolic function. Hartford et al., *Hypertension*, 6: 329-338 (1984). However, there is no close parallelism between blood pressure levels and cardiac hypertrophy. Although improvement in left ventricular function in response to antihypertensive therapy has been reported in humans, patients variously treated with a diuretic (hydrochlorothiazide), a β-blocker (propranolol), or a calcium channel blocker (diltiazem), have shown reversal of left ventricular hypertrophy, without improvement in diastolic function. Inouye et al., *Am. J. Cardiol.*, 53: 1583-7 (1984).

Another complex cardiac disease associated with cardiac hypertrophy is []hypertrophic cardiomyopathy[]. This condition is characterized by a great diversity of morphologic, functional, and clinical features (Maron et al., *N. Engl. J. Med.*, 316: 780-789 (1987); Spirito et al., *N. Engl. J. Med.*, 320: 749-755 (1989); Louie and Edwards, *Prog. Cardiovasc. Dis.*, 36: 275-308 (1994); Wigle et al., *Circulation*, 92: 1680-1692 (1995)), the heterogeneity of which is accentuated by the fact that it afflicts patients of all ages. Spirito et al., *N. Engl. J. Med.*, 336: 775-785 (1997). The causative factors of hypertrophic cardiomyopathy are also diverse and little understood. In general, mutations in genes encoding sarcomeric proteins are associated with hypertrophic cardiomyopathy. Recent data suggest that β-myosin heavy chain mutations may account for approximately 30 to 40 percent of cases of familial hypertrophic cardiomyopathy. Watkins et al., *N. Engl. J. Med.*, 326: 1108-1114 (1992); Schwartz et al, *Circulation*, 91: 532-540 (1995); Marian and Roberts, *Circulation*, 92: 1336-1347 (1995); Thierfelder et al., *Cell*, 77: 701-712 (1994); Watkins et al., *Nat. Gen.*, 11: 434-437 (1995). Besides β-myosin heavy chain, other locations of genetic mutations include cardiac troponin T, alpha topomyosin, cardiac myosin binding protein C, essential myosin light chain, and regulatory myosin light chain. See Malik and Watkins, *Curr. Opin. Cardiol.*, 12: 295-302 (1997).

Supravalvular []aortic stenosis[] is an inherited vascular disorder characterized by narrowing of the ascending aorta, but other arteries, including the pulmonary arteries, may also be affected. Untreated aortic stenosis may lead to increased intracardiac pressure resulting in myocardial hypertrophy and eventually heart failure and death. The pathogenesis of this disorder is not fully understood, but hypertrophy and possibly hyperplasia of medial smooth muscle are prominent features of this disorder. It has been reported that molecular variants of the elastin gene are involved in the development and pathogenesis of aortic stenosis. U.S. Pat. No. 5,650,282 issued Jul. 22, 1997.

[]Valvular regurgitation[] occurs as a result of heart diseases resulting in disorders of the cardiac valves. Various diseases, like rheumatic fever, can cause the shrinking or pulling apart of the valve orifice, while other diseases may result in endocarditis, an inflammation of the endocardium or lining membrane of the atrioventricular orifices and operation of the heart. Defects such as the narrowing of the valve stenosis or the defective closing of the valve result in an accumulation of blood in the heart cavity or regurgitation of blood past the valve. If uncorrected, prolonged valvular stenosis or insufficiency may result in cardiac hypertrophy and associated damage to the heart muscle, which may eventually necessitate valve replacement.

The treatment of all these, and other cardiovascular and endothelial disorders, which may or may not be accompanied by cardiac hypertrophy, is encompassed by the present invention.

The terms "cancer", "cancerous", and "malignant" refer to or describe the physiological condition in mammals that is typically characterized by unregulated cell growth. Examples of cancer include but are not limited to, carcinoma including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin[]s and non-Hodgkin[]s lymphoma, pancreatic cancer, glioblastoma, cervical cancer, ovarian cancer, liver cancer such as hepatic carcinoma and hepatoma, bladder cancer, breast cancer, colon cancer, colorectal cancer, endometrial carcinoma, salivary gland carcinoma, kidney cancer such as renal cell carcinoma and Wilms[] tumors, basal cell carcinoma, melanoma, prostate cancer, vulval cancer, thyroid cancer, testicular cancer, esophageal cancer, and various types of head and neck cancer. The preferred cancers for treatment herein are breast, colon, lung, melanoma, ovarian, and others involving vascular tumors as noted above.

The term "cytotoxic agent" as used herein refers to a substance that inhibits or prevents the function of cells and/or causes destruction of cells.

The term is intended to include radioactive isotopes (e.g., $^{131}$I, $^{125}$I, $^{90}$Y, and $^{186}$Re), chemotherapeutic agents, and toxins such as enzymatically active toxins of bacterial, fungal, plant, or animal origin, or fragments thereof.

A "chemotherapeutic agent" is a chemical compound useful in the treatment of cancer. Examples of chemotherapeutic agents include alkylating agents, folic acid antagonists, anti-metabolites of nucleic acid metabolism, antibiotics, pyrimidine analogs, 5-fluorouracil, cisplatin, purine nucleosides, amines, amino acids, triazol nucleosides, or corticosteroids. Specific examples include Adriamycin, Doxorubicin, 5-Fluorouracil, Cytosine arabinoside ("Ara-C"), Cyclophosphamide, Thiotepa, Busulfan, Cytoxin, Taxol, Toxotere, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (see U.S. Pat. No. 4,675,187), Melphalan, and other related nitrogen mustards. Also included in this definition are hormonal agents that act to regulate or inhibit hormone action on tumors, such as tamoxifen and onapristone.

A "growth-inhibitory agent" when used herein refers to a compound or composition that inhibits growth of a cell, such as an Wnt-overexpressing cancer cell, either in vitro or in vivo. Thus, the growth-inhibitory agent is one which significantly reduces the percentage of malignant cells in S phase.

Examples of growth-inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. Additional examples include tumor necrosis factor (TNF), an antibody capable of inhibiting or neutralizing the angiogenic activity of acidic or basic FGF or hepatocyte growth factor (HGF), an antibody capable of inhibiting or neutralizing the coagulant activities of tissue factor, protein C, or protein (see WO 91/01753, published Feb. 21, 1991), or an antibody capable of binding to HER2 receptor (WO 89/06692), such as the 4D5 antibody (and functional equivalents thereof) (e.g., WO 92/22653).

"Treatment" is an intervention performed with the intention of preventing the development or altering the pathology of a cardiovascular, endothelial, or angiogenic disorder. The concept of treatment is used in the broadest sense, and specifically includes the prevention (prophylaxis), moderation, reduction, and curing of cardiovascular, endothelial, or angiogenic disorders of any stage. Accordingly, "treatment" refers to both therapeutic treatment and prophylactic or preventative measures, wherein the object is to prevent or slow down (lessen) a cardiovascular or endothelial disorder, such as hypertrophy, or an angiogenic disorder, such as cancer. Those in need of treatment include those already with the disorder as well as those prone to have the disorder or those in whom the disorder is to be prevented. The disorder may result from any cause, including idiopathic, cardiotrophic, or myotrophic causes, or ischemia or ischemic insults, such as myocardial infarction.

"Chronic" administration refers to administration of the agent(s) in a continuous mode as opposed to an acute mode, so as to maintain the initial effect, such as an anti-hypertrophic effect, for an extended period of time.

"Mammal" for purposes of treatment refers to any animal classified as a mammal, including humans, domestic and farm animals, and zoo, sports, or pet animals, such as dogs, horses, cats, cows, sheep, pigs, etc. Preferably, the mammal is human.

Administration []in combination with[] one or more further therapeutic agents includes simultaneous (concurrent) and consecutive administration in any order.

The phrase "cardiovascular or endothelial agents[] refers generically to any drug that acts in treating cardiovascular and/or endothelial disorders.

Examples of cardiovascular agents are those that promote vascular homeostasis by modulating blood pressure, heart rate, heart contractility, and endothelial and smooth muscle biology, all of which factors have a role in cardiovascular disease. Specific examples of these include angiotensin-II receptor antagonists; endothelin receptor antagonists such as, for example, BOSENTAN™ and MOXONODIN™; interferon-gamma (IFN-γ); des-aspartate-angiotensin I; thrombolytic agents, e.g., streptokinase, urokinase, t-PA, and a t-PA variant specifically designed to have longer half-life and very high fibrin specificity, TNK t-PA (a T103N, N117Q, KHRR(296-299)AAAA t-PA variant, Keyt et al., *Proc. Natl. Acad. Sci. USA* 91, 3670-3674 (1994)); inotropic or hypertensive agents such as digoxigenin and β-adrenergic receptor blocking agents, e.g., propranolol, timolol, tertalolol, carteolol, nadolol, betaxolol, penbutolol, acetobutolol, atenolol, metoprolol, and carvedilol; angiotensin converting enzyme (ACE) inhibitors, e.g., quinapril, captopril, enalapril, ramipril, benazepril, fosinopril, and lisinopril; diuretics, e.g., chorothiazide, hydrochlorothiazide, hydroflumethazide, methylchlothiazide, benzthiazide, dichlorphenamide, acetazolamide, and indapamide; and calcium channel blockers, e.g., diltiazem, nifedipine, verapamil, nicardipine. One preferred category of this type is a therapeutic agent used for the treatment of cardiac hypertrophy or of a physiological condition instrumental in the development of cardiac hypertrophy, such as elevated blood pressure, aortic stenosis, or myocardial infarction.

"Angiogenic agents" and "endothelial agents" are active agents that promote angiogenesis and endothelial cell growth, respectively, or, if applicable, vasculogenesis. This would include factors that accelerate wound healing, such as growth hormone, insulin-like growth factor-I (IGF-I), VEGF, VIGF, PDGF, epidermal growth factor (EGF), CTGF and members of its family, FGF, and TGF-α and TGF-β.

"Angiostatic agents" are active agents that inhibit angiogenesis or vasculogenesis or otherwise inhibit or prevent growth of cancer cells. Examples include antibodies or other antagonists to angiogenic agents as defined above, such as antibodies to VEGF. They additionally include cytotherapeutic agents such as cytotoxic agents, chemotherapeutic agents, growth-inhibitory agents, apoptotic agents, and other agents to treat cancer, such as anti-HER-2, anti-CD20, and other bioactive and organic chemical agents.

In a pharmacological sense, in the context of the present invention, a "therapeutically effective amount" of an active agent (VEGF-E polypeptide or antagonist thereto) refers to an amount effective in the treatment of a cardiovascular, endothelial, and angiogenic disorder.

The term "antagonist" is used in the broadest sense, and includes any molecule that partially or fully blocks, inhibits, or neutralizes one or more of the biological activities of a native VEGF-E polypeptide disclosed herein, for example, if applicable, its mitogenic or angiogenic activity. Antagonists of VEGF-E polypeptide may act by interfering with the binding of the VEGF-E polypeptide to a cellular receptor, by incapacitating or killing cells that have been activated by VEGF-E polypeptide, or by interfering with vascular endothelial cell activation after VEGF-E polypeptide binding to a cellular receptor. All such points of intervention by a VEGF-E polypeptide antagonist shall be considered equivalent for purposes of this invention. The antagonists inhibit the mitogenic, angiogenic, or other biological activity of VEGF-E polypeptide, and thus are useful for the treatment of diseases or disorders characterized by undesirable excessive neovascularization, including by way of example tumors, and especially solid malignant tumors, rheumatoid arthritis, psoriasis, atherosclerosis, diabetic and other retinopathies, retrolental fibroplasia, age-related macular degeneration, neovascular glaucoma, hemangiomas, thyroid hyperplasias (including Grave's disease), corneal and other tissue transplantation, and chronic inflammation. The antagonists also are useful for the treatment of diseases or disorders characterized by undesirable excessive vascular permeability, such as edema associated with brain tumors, ascites associated with malignancies, Meigs' syndrome, lung inflammation, nephrotic syndrome, pericardial effusion (such as that associated with pericarditis), and pleural effusion.

In a similar manner, the term "agonist" is used in the broadest sense and includes any molecule that mimics a biological activity of a native VEGF-E polypeptide disclosed herein. Suitable agonist or antagonist molecules specifically include agonist or antagonist antibodies or antibody fragments, fragments, or amino acid sequence variants of native VEGF-E polypeptides, peptides, small organic molecules, etc.

A "small molecule" is defined herein to have a molecular weight below about 500 daltons.

The term []VEGF-E polypeptide receptor" as used herein refers to a cellular receptor for VEGF-E polypeptide, ordinarily a cell-surface receptor found on vascular endothelial cells, as well as variants thereof that retain the ability to bind VEGF-E polypeptide.

The term "antibody" is used in the broadest sense and specifically covers single anti-VEGF-E polypeptide monoclonal antibodies (including agonist, antagonist, and neutralizing antibodies) and anti-VEGF-E antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Active" or "activity" for the purposes herein refers to form(s) of VEGF-E which retain the biologic activities of native or naturally-occurring VEGF-E polypeptide.

Hybridization is preferably performed under "stringent conditions" which means (1) employing low ionic strength and high temperature for washing, for example, 0.015 sodium chloride/0.0015 M sodium citrate/0.1% sodium dodecyl sulfate at 50° C., or (2) employing during hybridization a denaturing agent, such as formamide, for example, 50% (vol/vol) formamide with 0.1% bovine serum albumin/0.1% Ficoll/0.1% polyvinylpyrrolidone/50 nM sodium phosphate buffer at pH 6.5 with 750 mM sodium chloride, 75 mM sodium citrate at 42° C. Another example is use of 50% formamide, 5×SSC (0.75 M NaCl, 0.075 M sodium citrate), 50 mM sodium phosphate (pH 6/8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS. Yet another example is hybridization using a buffer of 10% dextran sulfate, 2×SSC (sodium chloride/sodium citrate) and 50% formamide at 55° C., followed by a high-stringency wash consisting of 0.1×SSC containing EDTA at 55° C. Other conditions previously described and well known can be used to arrive at high, low or moderate stringencies. When a nucleic acid sequence of a nucleic acid molecule is provided, other nucleic acid molecules hybridizing thereto under the conditions described above are considered within the scope of the sequence. Preferably, the nucleic acid sequence of a nucleic acid molecule as provided herein has 70% or 80% nucleic acid sequence identity to SEQ ID NO:1, positions 259 through 1293. Most preferably, the nucleic acid sequence has 90% or 95% nucleic acid identity to SEQ ID NO:1, positions 259 through 1293.

"Transfection" refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

"Transformation" means introducing nucleic acid into an organism so that the nucleic acid is replicable, either as an extrachromosomal element or by chromosomal integrant. Depending on the host cell used, transformation is done using standard techniques appropriate to such cells. The calcium treatment employing calcium chloride, as described by Cohen, *Proc. Natl. Acad. Sci. (USA)*, 69: 2110 (1972) and Mandel et al., *J. Mol. Biol.*, 53: 154 (1970), is generally used for prokaryotes or other cells that contain substantial cell-wall barriers. For mammalian cells without such cell walls, the calcium phosphate precipitation method of Graham and van der Eb, *Virology*, 52: 456-457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.*, 130: 946 (1977) and Hsiao et al., *Proc. Natl. Acad. Sci. (USA)*, 76: 3829 (1979). However, other methods for introducing nucleic acid into cells such as by nuclear injection or by protoplast fusion may also be used.

"Site-directed mutagenesis" is a technique standard in the art, and is conducted using a synthetic oligonucleotide primer complementary to a single-stranded phage nucleic acid to be mutagenized except for limited mismatching, representing the desired mutation. Briefly, the synthetic oligonucleotide is used as a primer to direct synthesis of a strand complementary to the phage, and the resulting double-stranded nucleic acid is transformed into a phage-supporting host bacterium. Cultures of the transformed bacteria are plated in top agar, permitting plaque formation from single cells that harbor the phage. Theoretically, 50% of the new plaques will contain the phage having, as a single strand, the mutated form; 50% will have the original sequence. The plaques are hybridized with kinased synthetic primer at a temperature that permits hybridization of an exact match, but at which the mismatches with the original strand are sufficient to prevent hybridization. Plaques that hybridize with the probe are then selected and cultured, and the nucleic acid is recovered.

"Operably linked" refers to juxtaposition such that the normal function of the components can be performed. Thus, a coding sequence "operably linked" to control sequences refers to a configuration wherein the coding sequence can be expressed under the control of these sequences and wherein the DNA sequences being linked are contiguous and, in the case of a secretory leader, contiguous and in reading phase. For example, nucleic acid for a presequence or secretory leader is operably linked to nucleic acid for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Linking is accomplished by ligation at convenient restriction sites. If such sites do not exist, then synthetic oligonucleotide adaptors or linkers are used in accord with conventional practice.

"Control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. To effect transformation, the expression system may be included on a vector; however, the relevant DNA may then also be integrated into the host chromosome.

As used herein, "cell," "cell line," and "cell culture" are used interchangeably and all such designations include progeny. Thus, "transformants" or "transformed cells" includes the primary subject cell and cultures derived there-from without regard for the number of transfers. It is also understood that all progeny may not be precisely identical in DNA content, due to deliberate or inadvertent mutations. Mutant progeny that have the same functionality as screened for in the originally transformed cell are included. Where distinct designations are intended, it will be clear from the context.

"Plasmids" are designated by a lower case p preceded and/or followed by capital letters and/or numbers. The starting plasmids herein are commercially available, are publicly available on an unrestricted basis, or can be constructed from such available plasmids in accord with published procedures.

In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the site for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 mg of plasmid or DNA fragment is used with about 1-2 units of enzyme in about 20 ml of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction-cleaved ends of a DNA fragment from "circularizing" or forming a closed loop that would impede insertion of another DNA fragment at the restriction site. Unless otherwise stated, digestion of plasmids is not followed by 5'-terminal dephosphorylation. Procedures and reagents for dephosphorylation are conventional (Maniatis et al., *Molecular Cloning: A Laboratory Manual* (New York: Cold Spring Harbor Laboratory, 1982), pp. 133-134).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al., *Nucleic Acids Res.*, 9: 6103-6114 (1981), and Goeddel et al., *Nucleic Acids Res.*, 8, 4057 (1980).

"Southern Analysis" is a method by which the presence of DNA sequences in a digest or DNA-containing composition is confirmed by hybridization to a known, labelled oligonucleotide or DNA fragment. For the purposes herein, unless otherwise provided, Southern analysis shall mean separation of digests on 1 percent agarose, denaturation, and transfer to nitrocellulose by the method of Southern, *J. Mol. Biol.*, 98: 503-517 (1975), and hybridization as described by Maniatis et al., *Cell*, 15: 687-701 (1978).

"Ligation" refers to the process of forming phosphodiester bonds between two double-stranded nucleic acid fragments (Maniatis et al., 1982, supra, p. 146). Unless otherwise provided, ligation may be accomplished using known buffers and conditions with 10 units of T4 DNA ligase ("ligase") per 0.5 mg of approximately equimolar amounts of the DNA fragments to be ligated.

"Preparation" of DNA from transformants means isolating plasmid DNA from microbial culture. Unless otherwise provided, the alkaline/SDS method of Maniatis et al. 1982, supra, p. 90, may be used.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP Pat. Pub. No. 266,032 published May 4, 1988, or via deoxynucleoside H-phosphonate intermediates as described by Froehler et al., *Nucl. Acids Res.*, 14: 5399-5407 (1986). They are then purified on polyacrylamide gels.

Inhibitors of VEGF-E include those which reduce or inhibit the activity or expression of VEGF-E and includes antisense molecules.

The abbreviation "KDR" refers to the kinase domain region of the VEGF molecule. VEGF-E has no homology with VEGF in this domain.

The abbreviation "FLT-1" refers to the FMS-like tyrosine kinase binding domain which is known to bind to the corresponding FLT-1 receptor. VEGF-E has no homology with VEGF in this domain.

II. Compositions and Methods of the Invention

A. Full-length VEGF-E Polypeptide

The present invention provides newly-identified and isolated nucleotide sequences encoding polypeptides referred to in the present application as VEGF-E. In particular, cDNA encoding a VEGF-E polypeptide has been identified and isolated, as disclosed in further detail in the Examples below. Using BLAST sequence alignment computer programs, the VEGF-E polypeptide was found to have certain sequence identity with VEGF and BMP1.

B. VEGF-E Variants

In addition to the full-length native-sequence VEGF-E polypeptide described herein, it is contemplated that VEGF-E variants can be prepared. VEGF-E variants can be prepared by introducing appropriate nucleotide changes into the VEGF-E-encoding DNA, or by synthesis of the desired VEGF-E polypeptide. Those skilled in the art will appreciate that amino acid changes may alter post-translational processes of the VEGF-E polypeptide, such as changing the number or position of glycosylation sites or altering the membrane-anchoring characteristics.

Variations in the native full-length sequence VEGF-E or in various domains of the VEGF-E polypeptide described herein, can be made, for example, using any of the techniques and guidelines for conservative and non-conservative mutations set forth, for instance, in U.S. Pat. No. 5,364,934. Variations may be a substitution, deletion, or insertion of one or more codons encoding the VEGF-E polypeptide that results in a change in the amino acid sequence of the VEGF-E polypeptide as compared with the native-sequence VEGF-E. Optionally the variation is by substitution of at least one amino acid with any other amino acid in one or more of the domains of the VEGF-E polypeptide. Guidance in determining which amino acid residue may be inserted, substituted, or deleted without adversely affecting the desired activity may be found by comparing the sequence of the VEGF-E polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions, or substitutions of amino acids in the sequence and testing the resulting variants for activity in the in vitro assays described in the Examples below.

The variations can be made using methods known in the art such as oligonucleotide-mediated (site-directed) mutagenesis, alanine scanning, and PCR mutagenesis. Site-directed mutagenesis (Carter et al., *Nucl. Acids Res.*, 13:4331 (1986); Zoller et al., *Nucl. Acids Res.*, 10:6487 (1987)), cassette mutagenesis (Wells et al., *Gene*, 34:315 (1985)), restriction selection mutagenesis (Wells et al., *Philos. Trans. R. Soc. London SerA*, 317:415 (1986)), or other known techniques can be performed on the cloned DNA to produce the VEGF-E-encoding variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, *The Proteins*, (W. H. Freeman & Co., N.Y.); Chothia, *J. Mol. Biol*., 150:1 (1976)). If alanine substitution does not yield adequate amounts of variant, an isoteric amino acid can be used.

C. Modifications of VEGF-E

Covalent modifications of VEGF-E polypeptides are included within the scope of this invention. One type of covalent modification includes reacting targeted amino acid residues of a VEGF-E polypeptide with an organic derivatizing agent that is capable of reacting with selected side chains or the N- or C-terminal residues of a VEGF-E polypeptide. Derivatization with bifunctional agents is useful, for instance, for crosslinking VEGF-E to a water-insoluble support matrix or surface for use in the method for purifying anti-VEGF-E antibodies, and vice-versa. Commonly used crosslinking agents include, e.g., 1,1-bis(diazoacetyl)-2-phenylethane, glutaraldehyde, N-hydroxy-succinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane, and agents such as methyl-3-((p-azidophenyl)dithio) pro-pioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W. H. Freeman & Co., San Francisco, pp. 79-86 (1983)), acetylation of the N-terminal amine, and amidation of any C-terminal carboxyl group.

Another type of covalent modification of the VEGF-E polypeptide included within the scope of this invention comprises altering the native glycosylation pattern of the polypeptide. "Altering the native glycosylation pattern" is intended for purposes herein to mean deleting one or more carbohydrate moieties found in native-sequence VEGF-E polypeptide, and/or adding one or more glycosylation sites that are not present in the native-sequence VEGF-E polypeptide.

Addition of glycosylation sites to VEGF-E polypeptides may be accomplished by altering the amino acid sequence thereof. The alteration may be made, for example, by the addition of, or substitution by, one or more serine or threonine residues to the native-sequence VEGF-E polypeptide (for O-linked glycosylation sites). The VEGF-E amino acid sequence may optionally be altered through changes at the DNA level, particularly by mutating the DNA encoding the VEGF-E polypeptide at preselected bases such that codons are generated that will translate into the desired amino acids.

Another means of increasing the number of carbohydrate moieties on the VEGF-E polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem*., pp. 259-306 (1981).

Removal of carbohydrate moieties present on the VEGF-E polypeptide may be accomplished chemically or enzymatically or by mutational substitution of codons encoding amino acid residues that serve as targets for glycosylation. Chemical deglycosylation techniques are known in the art and described, for instance, by Hakimuddin et al., *Arch. Biochem. Biophys*., 259:52 (1987) and by Edge et al., *Anal. Biochem*., 118:131 (1981). Enzymatic cleavage of carbohydrate moieties on polypeptides can be achieved by the use of a variety of endo- and exo-glycosidases as described by Thotakura et al., *Meth. Enzymol*., 138:350 (1987).

Another type of covalent modification of VEGF-E comprises linking the VEGF-E polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

VEGF-E polypeptides of the present invention may also be modified in a way to form chimeric molecules comprising a VEGF-E polypeptide fused to another, heterologous polypeptide or amino acid sequence. In one embodiment, such a chimeric molecule comprises a fusion of a VEGF-E polypeptide with a tag polypeptide which provides an epitope to which an anti-tag antibody can selectively bind. The epitope tag is generally placed at the amino- or carboxyl-terminus of the VEGF-E polypeptide. The presence of such epitope-tagged forms of a VEGF-E polypeptide can be detected using an antibody against the tag polypeptide. Also, provision of the epitope tag enables the VEGF-E polypeptide to be readily purified by affinity purification using an anti-tag antibody or another type of affinity matrix that binds to the epitope tag. In an alternative embodiment, the chimeric molecule may comprise a fusion of a VEGF-E polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al.,

*Mol. Cell. Biol.*, 8:2159-2165 (1988)); the c-myc tag and the 8F9, 3C7, 6E10, G4, B7 and 9E10 antibodies thereto (Evan et al., *Molecular and Cellular Biology*, 5:3610-3616 (1985)); and the Herpes Simplex virus glycoprotein D (gD) tag and its antibody (Paborsky et al., *Protein Engineering*, 3(6):547-553 (1990)). Other tag polypeptides include the Flag-peptide (Hopp et al., *BioTechnology*, 6:1204-1210 (1988)); the KT3 epitope peptide (Martin et al., *Science*, 255:192-194 (1992)); an α-tubulin epitope peptide (Skinner et al., *J. Biol. Chem.*, 266:15163-15166 (1991)); and the T7 gene 10 protein peptide tag (Lutz-Freyermuth et al., *Proc. Nati. Acad. Sci. USA*, 87:6393-6397 (1990)).

D. Preparation of VEGF-E

The description below relates primarily to production of VEGF-E by culturing cells transformed or transfected with a vector containing at least the coding nucleic acid shown in FIG. 1, beginning with the circled start codon and ending just prior to the stop codon. It is, of course, contemplated that alternative methods, which are well known in the art, may be employed to prepare VEGF-E polypeptides. For instance, the VEGF-E sequence, or portions thereof, may be produced by direct peptide synthesis using solid-phase techniques (see, e.g., Stewart et al., *Solid-Phase Peptide Synthesis*, W. H. Freeman Co., San Francisco, Calif. (1969); Merrifield, *J. Am. Chem. Soc.*, 85:2149-2154 (1963)). In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of VEGF-E polypeptides may be chemically synthesized separately and combined using chemical or enzymatic methods to produce a full-length VEGF-E polypeptide.

1. Isolation of DNA Encoding VEGF-E

DNA encoding a VEGF-E polypeptide may be obtained from a cDNA library prepared from tissue believed to possess the VEGF-E mRNA and to express it at a detectable level. Accordingly, human VEGF-E-encoding DNA can be conveniently obtained from a cDNA library prepared from human tissue, such as described in the Examples. The VEGF-E-encoding gene may also be obtained from a genomic library or by oligonucleotide synthesis.

Libraries can be screened with probes (such as antibodies to a VEGF-E polypeptide or oligonucleotides of at least about 17-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding VEGF-E is to use PCR methodology (Sambrook et al., supra; Dieffenbach et al., *PCR Primer:A Laboratory Manual* (Cold Spring Harbor Laboratory Press, 1995)).

The Examples below describe techniques for screening a cDNA library.

The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation, or enzyme labeling. Hybridization conditions, including low stringency, moderate stringency, and high stringency, are provided in Sambrook et al., 1989, supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as ALIGN, DNAstar, and INHERIT.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., 1989, supra, to detect precursors and processing intermediates of mRNA that may not have been reverse-transcribed into cDNA.

2. Selection and Transformation of Host Cells

Host cells are transfected or transformed with expression or cloning vectors described herein for VEGF-E polypeptide production and cultured in conventional nutrient media modified as appropriate for inducing promoters, selecting transformants, or amplifying the genes encoding the desired sequences. The culture conditions, such as media, temperature, pH, and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., 1989, supra.

Methods of transfection are known to the ordinarily skilled artisan, for example, $CaPO_4$ and electroporation. Depending on the host cell used, transformation is performed using standard techniques appropriate to such cells. The calcium treatment employing calcium chloride, as described in Sambrook et al., 1989, supra, or electroporation is generally used for prokaryotes or other cells that contain substantial cell-wall barriers. For mammalian cells without such cell walls, the calcium phosphate precipitation method of Graham and van der Eb, *Virology*, 52:456-457 (1978) can be employed. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene or polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for VEGF-E-encoding vectors. *Saccharomyces cerevisiae* is a commonly used lower eukaryotic host microorganism.

Suitable host cells for the expression of glycosylated VEGF-E are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding the desired VEGF-E polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The desired VEGF-E polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the VEGF-E-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010,182), or acid phosphatase leader, the C. albicans glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV, or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the VEGF-E-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 (Stinchcomb et al., *Nature*, 282:39 (1979); Kingsman et al., *Gene*, 7:141 (1979); Tschemper et al., *Gene*, 10:157 (1980)). The trp1 gene provides a selection marker for a mutant strain of yeast lacking the ability to grow in tryptophan, for example, ATCC No. 44076 or PEP4-1 (Jones, *Genetics*, 85:12 (1977)).

Expression and cloning vectors usually contain a promoter operably linked to the VEGF-E-encoding nucleic acid sequence to direct mRNA synthesis. Promoters recognized by a variety of potential host cells are well known. Promoters suitable for use with prokaryotic hosts include the β-lactamase and lactose promoter systems (Chang et al., *Nature*, 275:615 (1978); Goeddel et al., *Nature*, 281:544 (1979)), alkaline phosphatase, a tryptophan (trp) promoter system (Goeddel, *Nucleic Acids Res.*, 8:4057 (1980); EP 36,776), and hybrid promoters such as the tac promoter (deBoer et al., *Proc. Natl. Acad. Sci. USA*, 80:21-25 (1983)). Promoters for use in bacterial systems also will contain a Shine-Dalgarno (S.D.) sequence operably linked to the DNA encoding the VEGF-E polypeptide.

Examples of suitable promoting sequences for use with yeast hosts include the promoters for 3-phosphoglycerate kinase (Hitzeman et al., *J. Biol. Chem.*, 255:2073 (1980)) or other glycolytic enzymes (Hess et al., *J. Adv. Enzyme Reg.*, 7:149 (1968); Holland, *Biochemistry*, 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

VEGF-E transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus, and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding a VEGF-E polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the VEGF-E coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding VEGF-E.

Still other methods, vectors, and host cells suitable for adaptation to the synthesis of VEGF-E polypeptides in recombinant vertebrate cell culture are described in Gething et al., *Nature*, 293:620-625 (1981); Mantei et al., *Nature*, 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA (Thomas, *Proc. Natl. Acad. Sci. USA*, 77:5201-5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native-sequence VEGF-E polypeptide or against a synthetic peptide based on the DNA sequences provided herein or against exogenous sequence fused to VEGF-E-encoding DNA and encoding a specific antibody epitope.

5. Purification of Polypeptide

Forms of VEGF-E may be recovered from culture medium or from host cell lysates. Cells employed in expression of VEGF-E polypeptides can be disrupted by various physical or chemical means, such as freeze-thaw cycling, sonication, mechanical disruption, or cell lysing agents. It may be desired to purify VEGF-E from recombinant cell proteins or polypeptides. The following procedures are exemplary of suitable purification procedures: by fractionation on an ion-exchange column; ethanol precipitation; reverse-phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal-chelating columns to bind epitope-tagged forms of the VEGF-E polypeptide. Various methods of protein purification may be employed and such methods are known in the art and described, for example, in Deutscher, *Methods in Enzymology*, 182 (1990); Scopes, *Protein Purification:Principles and Practice*, Springer-Verlag, New York (1982). The purification step(s) selected will depend, for example, on the nature of the production process used and the particular VEGF-E polypeptide produced.

Since VEGF-E may aggregate into dimers, it is within the scope hereof to provide hetero- and homodimers. Where one or more subunits are variants, the changes in amino acid sequence can be the same or different for each subunit chain. Heterodimers are readily produced by cotransforming host cells with DNA encoding both subunits and, if necessary, purifying the desired heterodimer, or by separately synthesizing the subunits, dissociating the subunits (e.g., by treatment with a chaotropic agent such as urea, guanidine hydrochloride, or the like), mixing the dissociated subunits, and then reassociating the subunits by dialyzing away the chaotropic agent.

E. Uses for VEGF-E and Formulations

1. Assays for Cardiovascular, Endothelial, and Angiogenic Activity

Various assays can be used to test the polypeptide herein for cardiovascular, endothelial, and angiogenic activity. Such assays include those provided in the Examples below.

Assays for testing for endothelin antagonist activity, as disclosed in U.S. Pat. No. 5,773,414, include a rat heart ventricle binding assay where the polypeptide is tested for its ability to inhibit iodinized endothelin-1 binding in a receptor assay, an endothelin receptor binding assay testing for intact cell binding of radiolabeled endothelin-1 using rabbit renal artery vascular smooth muscle cells, an inositol phosphate accumulation assay where functional activity is determined in Rat-1 cells by measuring intra-cellular levels of second messengers, an arachidonic acid release assay that measures the ability of added compounds to reduce endothelin-stimulated arachidonic acid release in cultured vascular smooth muscles, in vitro (isolated vessel) studies using endothelium from male New Zealand rabbits, and in vivo studies using male Sprague-Dawley rats. Assays for tissue generation activity include, without limitation, those described in WO 95/16035 (bone, cartilage, tendon); WO 95/05846 (nerve, neuronal), and WO 91/07491 (skin, endothelium).

Assays for wound-healing activity include, for example, those described in Winter, *Epidermal Wound Healing*, Maibach, H I and Rovee, D T, eds. (Year Book Medical Publishers, Inc., Chicago), pp. 71-112, as modified by the article of Eagistein and Mertz, *J. Invest. Dermatol.*, 71: 382-384 (1978).

An assay to screen for a test molecule relating to a VEGF-E polypeptide that binds an endothelin $B_1$ ($ETB_1$) receptor polypeptide and modulates signal transduction activity involves providing a host cell transformed with a DNA encoding endothelin $B_1$ receptor polypeptide, exposing the cells to the test candidate, and measuring endothelin $B_1$ receptor signal transduction activity, as described, e.g., in U.S. Pat. No. 5,773,223.

There are several cardiac hypertrophy assays. In vitro assays include induction of spreading of adult rat cardiac myocytes. In this assay, ventricular myocytes are isolated from a single (male Sprague-Dawley) rat, essentially following a modification of the procedure described in detail by Piper et al., Adult ventricular rat heart muscle cells in *Cell Culture Techniques in Heart and Vessel Research*, H. M. Piper, ed. (Berlin: Springer-Verlag, 1990), pp. 36-60. This procedure permits the isolation of adult ventricular myocytes and the long-term culture of these cells in the rod-shaped phenotype. Phenylephrine and Prostaglandin $F_{2\alpha}$ ($PGF_{2\alpha}$) have been shown to induce a spreading response in these adult cells. The inhibition of myocyte spreading induced by $PGF_{2\alpha}$ or $PGF_{2\alpha}$ analogs (e.g., fluprostenol) and phenylephrine by various potential inhibitors of cardiac hypertrophy is then tested.

One example of an in vivo assay is a test for inhibiting cardiac hypertrophy induced by fluprostenol in vivo. This pharmacological model tests the ability of the VEGF-E polypeptide to inhibit cardiac hypertrophy induced in rats (e.g., male Wistar or Sprague-Dawley) by subcutaneous injection of fluprostenol (an agonist analog of $PGF_{2\alpha}$). It is known that rats with pathologic cardiac hypertrophy induced by myocardial infarction have chronically elevated levels of extractable $PGF_{2\alpha}$ in their myocardium. Lai et al., *Am. J. Physiol.* (*Heart Circ. Physiol.*), 271: H2197-H2208 (1996). Accordingly, factors that can inhibit the effects of fluprostenol on myocardial growth in vivo are potentially useful for treating cardiac hypertrophy. The effects of the VEGF-E polypeptide on cardiac hypertrophy are determined by measuring the weight of heart, ventricles, and left ventricle (normalized by body weight) relative to fluprostenol-treated rats not receiving the VEGF-E polypeptide.

Another example of an in vivo assay is the pressure-overload cardiac hypertrophy assay. For in vivo testing it is common to induce pressure-overload cardiac hypertrophy by constriction of the abdominal aorta of test animals. In a typical protocol, rats (e.g., male Wistar or Sprague-Dawley) are treated under anesthesia, and the abdominal aorta of each rat is narrowed down just below the diaphragm. Beznak M., Can. *J. Biochem. Physiol.*, 33: 985-94 (1955). The aorta is exposed through a surgical incision, and a blunted needle is placed next to the vessel. The aorta is constricted with a ligature of silk thread around the needle, which is immediately removed and which reduces the lumen of the aorta to the diameter of the needle. This approach is described, for example, in Rossi et al., *Am. Heart J.*, 124: 700-709 (1992) and ORourke and Reibel, *P.S.E.M.B.*, 200: 95-100 (1992).

In yet another in vivo assay, the effect on cardiac hypertrophy following experimentally induced myocardial infarction (MI) is measured. Acute MI is induced in rats by left coronary artery ligation and confirmed by electrocardiographic examination. A sham-operated group of animals is also prepared as control animals. Earlier data have shown that cardiac hypertrophy is present in the group of animals with MI, as evidenced by an 18% increase in heart weight-to-body weight ratio. Lai et al., supra. Treatment of these animals with candidate blockers of cardiac hypertrophy, e.g., VEGF-E polypeptide, provides valuable information about the therapeutic potential of the candidates tested. One further such assay test for induction of cardiac hypertrophy is disclosed in U.S. Pat. No. 5,773,415, using Sprague-Dawley rats.

For cancer, a variety of well-known animal models can be used to further understand the role of the genes identified herein in the development and pathogenesis of tumors, and to test the efficacy of candidate therapeutic agents, including antibodies and other antagonists of the native VEGF-E polypeptides, such as small-molecule antagonists. The in vivo nature of such models makes them particularly predictive of responses in human patients. Animal models of tumors and cancers (e.g., breast cancer, colon cancer, prostate cancer, lung cancer, etc.) include both non-recombinant and recombinant (transgenic) animals. Non-recombinant animal models include, for example, rodent, e.g., murine models. Such models can be generated by introducing tumor cells into syngeneic mice using standard techniques, e.g., subcutaneous injection, tail vein injection, spleen implantation, intraperitoneal implantation, implantation under the renal capsule, or orthopin implantation, e.g., colon cancer cells implanted in colonic tissue. See, e.g., PCT publication No. WO 97/33551, published Sep. 18, 1997.

Probably the most often used animal species in oncological studies are immunodeficient mice and, in particular, nude mice. The observation that the nude mouse with thymic hypo/aplasia could successfully act as a host for human tumor xenografts has lead to its widespread use for this purpose. The autosomal recessive nu gene has been introduced into a very large number of distinct congenic strains of nude mouse, including, for example, ASW, A/He, AKR, BALB/c, B10.LP, C17, C3H, C57BL, C57, CBA, DBA, DDD, I/st, NC, NFR, NFS, NFS/N, NZB, NZC, NZW, P, RIII, and SJL. In addition, a wide variety of other animals with inherited immunological defects other than the nude mouse have been bred and used as recipients of tumor xenografts. For further details see, e.g., *The Nude Mouse in Oncology Research*, E. Boven and B. Winograd, eds. (CRC Press, Inc., 1991).

The cells introduced into such animals can be derived from known tumor/cancer cell lines, such as any of the above-listed tumor cell lines, and, for example, the B104-1-1 cell line (stable NIH-3T3 cell line transfected with the neu protooncogene); ras-transfected NIH-3T3 cells; Caco-2 (ATCC HTB-37); or a moderately well-differentiated grade II human colon adenocarcinoma cell line, HT-29 (ATCC HTB-38); or from tumors and cancers. Samples of tumor or cancer cells can be obtained from patients undergoing surgery, using standard conditions involving freezing and storing in liquid nitrogen. Karmali et al., *Br. J. Cancer*, 48: 689-696 (1983). Tumor cells can be introduced into animals such as nude mice by a variety of procedures. The subcutaneous (s.c.) space in mice is very suitable for tumor implantation. Tumors can be transplanted s.c. as solid blocks, as needle biopsies by use of a trochar, or as cell suspensions. For solid-block or trochar implantation, tumor tissue fragments of suitable size are introduced into the s.c. space. Cell suspensions are freshly prepared from primary tumors or stable tumor cell lines, and injected subcutaneously. Tumor cells can also be injected as subdermal implants. In this location, the inoculum is deposited between the lower part of the dermal connective tissue and the s.c. tissue.

Animal models of breast cancer can be generated, for example, by implanting rat neuroblastoma cells (from which the neu oncogene was initially isolated), or neu-transformed NIH-3T3 cells into nude mice, essentially as described by Drebin et al. *Proc. Nat. Acad. Sci. USA*, 83: 9129-9133 (1986).

Similarly, animal models of colon cancer can be generated by passaging colon cancer cells in animals, e.g., nude mice, leading to the appearance of tumors in these animals. An orthotopic transplant model of human colon cancer in nude mice has been described, for example, by Wang et al., *Cancer Research*, 54: 4726-4728 (1994) and Too et al., *Cancer Research*, 55: 681-684 (1995). This model is based on the so-called []METAMOUSE[]™ sold by AntiCancer, Inc. (San Diego, Calif.).

Tumors that arise in animals can be removed and cultured in vitro. Cells from the in vitro cultures can then be passaged to animals. Such tumors can serve as targets for further testing or drug screening. Alternatively, the tumors resulting from the passage can be isolated and RNA from pre-passage cells and cells isolated after one or more rounds of passage analyzed for differential expression of genes of interest. Such passaging techniques can be performed with any known tumor or cancer cell lines.

For example, Meth A, CMS4, CMS5, CMS21, and WEHI-164 are chemically induced fibrosarcomas of BALB/c female mice (DeLeo et al., *J. Exp. Med.*, 146: 720 (1977)), which provide a highly controllable model system for studying the anti-tumor activities of various agents. Palladino et al., *J. Immunol.*, 138: 4023-4032 (1987). Briefly, tumor cells are propagated in vitro in cell culture. Prior to injection into the animals, the cell lines are washed and suspended in buffer, at a cell density of about $10 \times 10^6$ to $10 \times 10^7$ cells/ml. The animals are then infected subcutaneously with 10 to 100 µl of the cell suspension, allowing one to three weeks for a tumor to appear.

In addition, the Lewis lung (3LL) carcinoma of mice, which is one of the most thoroughly studied experimental tumors, can be used as an investigational tumor model. Efficacy in this tumor model has been correlated with beneficial effects in the treatment of human patients diagnosed with small-cell carcinoma of the lung (SCCL). This tumor can be introduced in normal mice upon injection of tumor fragments from an affected mouse or of cells maintained in culture. Zupi et al., *Br. J. Cancer*, 41: suppl. 4, 30 (1980). Evidence indicates that tumors can be started from injection of even a single cell and that a very high proportion of infected tumor cells survive. For further information about this tumor model see Zacharski, *Haemostasis*, 16: 300-320 (1986).

One way of evaluating the efficacy of a test compound in an animal model with an implanted tumor is to measure the size of the tumor before and after treatment. Traditionally, the size of implanted tumors has been measured with a slide caliper in two or three dimensions. The measure limited to two dimensions does not accurately reflect the size of the tumor; therefore, it is usually converted into the corresponding volume by using a mathematical formula. However, the measurement of tumor size is very inaccurate. The therapeutic effects of a drug candidate can be better described as treatment-induced growth delay and specific growth delay. Another important variable in the description of tumor growth is the tumor volume doubling time. Computer programs for the calculation and description of tumor growth are also available, such as the program reported by Rygaard and Spang-Thomsen, *Proc. 6th Int. Workshop on Immune-Deficient Animals*, Wu and Sheng eds. (Basel, 1989), p. 301. It is noted, however, that necrosis and inflammatory responses following treatment may actually result in an increase in tumor size, at least initially. Therefore, these changes need to be carefully monitored, by a combination of a morphometric method and flow cytometric analysis.

Further, nucleic acids that encode VEGF-E polypeptide or any of its modified forms can also be used to generate either transgenic animals or "knock-out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. Hence, recombinant (transgenic) animal models can be engineered by introducing the coding portion of the genes encoding VEGF-E identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g., baboons, chimpanzees and monkeys. In one embodiment, cDNA encoding VEGF-E polypeptide can be used to clone genomic DNA encoding VEGF-E in accordance with established techniques and the genomic sequences used to generate transgenic animals that contain cells which express DNA encoding VEGF-E. Techniques known in the art to introduce a transgene into such animals include pronucleic microinjection (U.S. Pat. No. 4,873,191); retrovirus-mediated gene transfer into germ lines (e.g., Van der Putten et al., *Proc. Natl. Acad. Sci. USA*, 82: 6148-615 (1985)); gene targeting in embryonic stem cells (Thompson et al., *Cell*, 56: 313-321 (1989)); electroporation of embryos (Lo, *Mol. Cell. Biol.*, 3: 1803-1814 (1983)); and sperm-mediated gene transfer. Lavitrano et al., *Cell*, 57: 717-73 (1989). For a review, see, for example, U.S. Pat. No. 4,736,866. Methods for generating transgenic animals, particularly animals such as mice or rats, have become conventional in the art and are described, for example, in U.S. Pat. Nos. 4,736,866 and 4,870,009. Typically, particular cells would be targeted for VEGF-E transgene incorporation with tissue-specific enhancers. Transgenic animals that include a copy of a transgene encoding VEGF-E introduced into the germ line of the animal at an embryonic stage can be used to examine the effect of increased expression of DNA encoding VEGF-E. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

For the purpose of the present invention, transgenic animals include those that carry the transgene only in part of their cells ([]mosaic animals[]). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA*, 89: 6232-636 (1992). The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry. The animals are further examined for signs of tumor or cancer development.

Alternatively, "knock-out" animals can be constructed that have a defective or altered gene encoding a VEGF-E polypeptide identified herein, as a result of homologous recombination between the endogenous gene encoding the VEGF-E polypeptide and altered genomic DNA encoding the same polypeptide introduced into an embryonic cell of the animal. For example, cDNA encoding a particular VEGF-E polypeptide can be used to clone genomic DNA encoding that polypeptide in accordance with established techniques. A portion of the genomic DNA encoding a particular VEGF-E polypeptide can be deleted or replaced with another gene, such as a gene encoding a selectable marker that can be used to monitor integration. Typically, several kilobases of unaltered flanking DNA (both at the 5' and 3' ends) are included in the vector. See, e.g., Thomas and Capecchi, *Cell*, 51: 503 (1987) for a description of homologous recombination vectors. The vector is introduced into an embryonic stem cell line (e.g., by electroporation) and cells in which the introduced DNA has homologously recombined with the endogenous DNA are selected. See, e.g., Li et al., *Cell*, 69: 915 (1992). The selected cells are then injected into a blastocyst of an animal (e.g., a mouse or rat) to form aggregation chimeras. See, e.g., Bradley, in *Teratocarcinomas and Embryonic Stem Cells: A Practical Approach*, E. J. Robertson, ed. (IRL: Oxford, 1987), pp. 113-152. A chimeric embryo can then be implanted into a suitable pseudopregnant female foster animal and the embryo brought to term to create a "knock-out" animal. Progeny harboring the homologously recombined DNA in their germ cells can be identified by standard techniques and used to breed animals in which all cells of the animal contain the homologously recombined DNA. Knockout animals can be characterized, for instance, by their ability to defend against certain pathological conditions and by their development of pathological conditions due to absence of the VEGF-E polypeptide.

The efficacy of antibodies specifically binding the VEGF-E polypeptides identified herein, and other drug candidates, can be tested also in the treatment of spontaneous animal tumors. A suitable target for such studies is the feline oral squamous cell carcinoma (SCC). Feline oral SCC is a highly invasive, malignant tumor that is the most common oral malignancy of cats, accounting for over 60% of the oral tumors reported in this species. It rarely metastasizes to distant sites, although this low incidence of metastasis may merely be a reflection of the short survival times for cats with this tumor. These tumors are usually not amenable to surgery, primarily because of the anatomy of the feline oral cavity. At present, there is no effective treatment for this tumor. Prior to entry into the study, each cat undergoes complete clinical examination and biopsy, and is scanned by computed tomography (CT). Cats diagnosed with sublingual oral squamous cell tumors are excluded from the study. The tongue can become paralyzed as a result of such tumor, and even if the treatment kills the tumor, the animals may not be able to feed themselves. Each cat is treated repeatedly, over a longer period of time. Photographs of the tumors will be taken daily during the treatment period, and at each subsequent recheck. After treatment, each cat undergoes another CT scan. CT scans and thoracic radiograms are evaluated every 8 weeks thereafter. The data are evaluated for differences in survival, response, and toxicity as compared to control groups. Positive response may require evidence of tumor regression, preferably with improvement of quality of life and/or increased life span.

In addition, other spontaneous animal tumors, such as fibrosarcoma, adenocarcinoma, lymphoma, chondroma, or leiomyosarcoma of dogs, cats, and baboons can also be tested. Of these, mammary adenocarcinoma in dogs and cats is a preferred model as its appearance and behavior are very similar to those in humans. However, the use of this model is limited by the rare occurrence of this type of tumor in animals.

Other in vitro and in vivo cardiovascular, endothelial, and angiogenic tests known in the art are also suitable herein.

2. Tissue Distribution

The results of the cardiovascular, endothelial, and angiogenic assays herein can be verified by further studies, such as by determining mRNA expression in various human tissues.

As noted before, gene amplification and/or gene expression in various tissues may be measured by conventional Southern blotting, Northern blotting to quantitate the transcription of mRNA (Thomas, *Proc. Natl. Acad. Sci. USA*, 77:5201-5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes.

Gene expression in various tissues, alternatively, may be measured by immunological methods, such as immunohistochemical staining of tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native-sequence VEGF-E polypeptide or against a synthetic peptide based on the DNA sequences provided herein or against exogenous sequence fused to DNA encoding VEGF-E and encoding a specific antibody epitope. General techniques for generating antibodies, and special protocols for in situ hybridization are provided hereinbelow.

3. Antibody Binding Studies

The results of the cardiovascular, endothelial, and angiogenic study can be further verified by antibody binding studies, in which the ability of anti-VEGF-E antibodies to inhibit the effect of the VEGF-E polypeptides on endothelial cells or other cells used in the cardiovascular, endothelial, and angiogenic assays is tested. Exemplary antibodies include polyclonal, monoclonal, humanized, bispecific, and heteroconjugate antibodies, the preparation of which will be described hereinbelow.

Antibody binding studies may be carried out in any known assay method, such as competitive binding assays, direct and indirect sandwich assays, and immunoprecipitation assays. Zola, *Monoclonal Antibodies: A Manual of Techniques* (CRC Press, Inc., 1987), pp.147-158.

Competitive binding assays rely on the ability of a labeled standard to compete with the test sample analyte for binding with a limited amount of antibody. The amount of target protein in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte that remain unbound.

Sandwich assays involve the use of two antibodies, each capable of binding to a different immunogenic portion, or epitope, of the protein to be detected. In a sandwich assay, the test sample analyte is bound by a first antibody that is immobilized on a solid support, and thereafter a second antibody binds to the analyte, thus forming an insoluble three-part complex. See, e.g., US Pat No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tissue sample may be fresh or frozen or may be embedded in paraffin and fixed with a preservative such as formalin, for example.

4. Cell-Based Tumor Assays

Cell-based assays and animal models for cardiovascular, endothelial, and angiogenic disorders, such as tumors, can be used to verify the findings of a cardiovascular, endothelial, and angiogenic assay herein, and further to understand the relationship between the genes identified herein and the development and pathogenesis of undesirable cardiovascular, endothelial, and angiogenic cell growth. The role of gene products identified herein in the development and pathology of undesirable cardiovascular, endothelial, and angiogenic cell growth, e.g., tumor cells, can be tested by using cells or cells lines that have been identified as being stimulated or inhibited by the VEGF-E polypeptide herein. Such cells include, for example, those set forth in the Examples below.

In a different approach, cells of a cell type known to be involved in a particular cardiovascular, endothelial, and angiogenic disorder are transfected with the cDNAs herein, and the ability of these cDNAs to induce excessive growth or inhibit growth is analyzed. If the cardiovascular, endothelial, and angiogenic disorder is cancer, suitable tumor cells include, for example, stable tumor cells lines such as the B104-1-1 cell line (stable NIH-3T3 cell line transfected with the neu protooncogene) and ras-transfected NIH-3T3 cells, which can be transfected with the desired gene and monitored for tumorigenic growth. Such transfected cell lines can then be used to test the ability of poly- or monoclonal antibodies or antibody compositions to inhibit tumorigenic cell growth by exerting cytostatic or cytotoxic activity on the growth of the transformed cells, or by mediating antibody-dependent cellular cytotoxicity (ADCC). Cells transfected with the coding sequences of the genes identified herein can further be used to identify drug candidates for the treatment of cardiovascular, endothelial, and angiogenic disorders such as cancer.

In addition, primary cultures derived from tumors in transgenic animals (as described above) can be used in the cell-based assays herein, although stable cell lines are preferred. Techniques to derive continuous cell lines from transgenic animals are well known in the art. See, e.g., Small et al., *Mol. Cell. Biol.* 5: 642-648 (1985).

5. Gene Therapy

The VEGF-E polypeptide herein and polypeptidyl agonists and antagonists may be employed in accordance with the present invention by expression of such polypeptides in vivo, which is often referred to as gene therapy.

There are two major approaches to getting the nucleic acid (optionally contained in a vector) into the patient's cells: in vivo and ex vivo. For in vivo delivery the nucleic acid is injected directly into the patient, usually at the sites where the VEGF-E polypeptide is required, i.e., the site of synthesis of the VEGF-E polypeptide, if known, and the site (e.g., wound) where VEGF-E polypeptide biological activity is needed. For ex vivo treatment, the patient's cells are removed, the nucleic acid is introduced into these isolated cells, and the modified cells are administered to the patient either directly or, for example, encapsulated within porous membranes that are implanted into the patient (see, e.g., U.S. Pat. Nos. 4,892,538 and 5,283,187).

There are a variety of techniques available for introducing nucleic acids into viable cells. The techniques vary depending upon whether the nucleic acid is transferred into cultured cells in vitro, or transferred in vivo in the cells of the intended host. Techniques suitable for the transfer of nucleic acid into mammalian cells in vitro include the use of liposomes, electroporation, microinjection, transduction, cell fusion, DEAE-dextran, the calcium phosphate precipitation method, etc. Transduction involves the association of a replication-defective, recombinant viral (preferably retroviral) particle with a cellular receptor, followed by introduction of the nucleic acids contained by the particle into the cell. A commonly used vector for ex vivo delivery of the gene is a retrovirus.

The currently preferred in vivo nucleic acid transfer techniques include transfection with viral or non-viral vectors (such as adenovirus, lentivirus, Herpes simplex I virus, or adeno-associated virus (AAV)) and lipid-based systems (useful lipids for lipid-mediated transfer of the gene are, for example, DOTMA, DOPE, and DC-Chol; see, e.g., Tonkinson et al., *Cancer Investigation*, 14(1): 54-65 (1996)). The most preferred vectors for use in gene therapy are viruses, most preferably adenoviruses, AAV, lentiviruses, or retroviruses. A viral vector such as a retroviral vector includes at least one transcriptional promoter/enhancer or locus-defining element(s), or other elements that control gene expression by other means such as alternate splicing, nuclear RNA export, or post-translational modification of messenger. In addition, a viral vector such as a retroviral vector includes a nucleic acid molecule that, when transcribed in the presence of a gene encoding VEGF-E polypeptide, is operably linked thereto and acts as a translation initiation sequence. Such vector constructs also include a packaging signal, long terminal repeats (LTRs) or portions thereof, and positive and negative strand primer binding sites appropriate to the virus used (if these are not already present in the viral vector). In addition, such vector typically includes a signal sequence for secretion of the VEGF-E polypeptide from a host cell in which it is placed. Preferably the signal sequence for this purpose is a mammalian signal sequence, most preferably the native signal sequence for VEGF-E polypeptide. Optionally, the vector construct may also include a signal that directs polyadenylation, as well as one or more restriction sites and a translation termination sequence. By way of example, such vectors will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

In some situations, it is desirable to provide the nucleic acid source with an agent that targets the target cells, such as an antibody specific for a cell-surface membrane protein or the target cell, a ligand for a receptor on the target cell, etc. Where liposomes are employed, proteins that bind to a cell-surface membrane protein associated with endocytosis may be used for targeting and/or to facilitate uptake, e.g,. capsid proteins or fragments thereof tropic for a particular cell type, antibodies for proteins that undergo internalization in cycling, and proteins that target intracellular localization and enhance intracellular half-life. The technique of receptor-mediated endocytosis is described, for example, by Wu et al., *J. Biol. Chem.*, 262: 4429-4432 (1987); and Wagner et al., *Proc. Natl. Acad. Sci. USA*, 87: 3410-3414 (1990). For a review of the currently known gene marking and gene therapy protocols, see Anderson et al., *Science*, 256: 808-813 (1992). See also WO 93/25673 and the references cited therein.

Suitable gene therapy and methods for making retroviral particles and structural proteins can be found in, e.g., U.S. Pat. No. 5,681,746.

6. Use of Gene as Diagnostic

This invention is also related to the use of the gene encoding the VEGF-E polypeptide as a diagnostic. Detection of a mutated form of the VEGF-E polypeptide will allow a diagnosis of a cardiovascular, endothelial, and angiogenic disease or a susceptibility to a cardiovascular, endothelial, and angiogenic disease, such as a tumor, since mutations in the VEGF-E polypeptide may cause tumors.

Individuals carrying mutations in the gene encoding human VEGF-E polypeptide may be detected at the DNA level by a variety of techniques. Nucleic acids for diagnosis may be obtained from a patient's cells, such as from blood, urine, saliva, tissue biopsy, and autopsy material. The genomic DNA may be used directly for detection or may be amplified enzymatically by using PCR (Saiki et al., *Nature*, 324: 163-166 (1986)) prior to analysis. RNA or cDNA may also be used for the same purpose. As an example, PCR primers complementary to the nucleic acid encoding the VEGF-E polypeptide can be used to identify and analyze VEGF-E polypeptide mutations. For example, deletions and insertions can be detected by a change in size of the amplified product in comparison to the normal genotype. Point mutations can be identified by hybridizing amplified DNA to radiolabeled RNA encoding VEGF-E polypeptide, or alternatively, radiolabeled antisense DNA sequences encoding VEGF-E polypeptide. Perfectly matched sequences can be distinguished from mismatched duplexes by RNAse A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamidine gradient gels in which the mobilities of different DNA fragments are retarded in the gel at different positions according to their specific melting or partial melting temperatures. See, e.g., Myers et al., *Science*, 230: 1242 (1985).

Sequence changes at specific locations may also be revealed by nuclease protection assays, such as RNAse and S1 protection or the chemical cleavage method, for example, Cotton et al., *Proc. Natl. Acad. Sci. USA*, 85: 4397-4401 (1985).

Thus, the detection of a specific DNA sequence may be achieved by methods such as hybridization, RNAse protection, chemical cleavage, direct DNA sequencing, or the use of restriction enzymes, e.g., restriction fragment length polymorphisms (RFLP), and Southern blotting of genomic DNA.

7. Use to Detect VEGF-E Polypeptide Levels

In addition to more conventional gel-electrophoresis and DNA sequencing, mutations can also be detected by in situ analysis.

VEGF-E polypeptide expression may be linked to vascular disease or neovascularization associated with tumor formation. If the VEGF-E polypeptide has a signal sequence and the mRNA is highly expressed in endothelial cells and to a lesser extent in smooth muscle cells, this indicates that the VEGF-E polypeptide is present in serum. Accordingly, an anti-VEGF-E polypeptide antibody could be used to diagnose vascular disease or neovascularization associated with tumor formation, since an altered level of this VEGF-E polypeptide may be indicative of such disorders.

A competition assay may be employed wherein antibodies specific to the VEGF-E polypeptide are attached to a solid support and labeled VEGF-E polypeptide and a sample derived from the host are passed over the solid support and the amount of label detected attached to the solid support can be correlated to a quantity of VEGF-E polypeptide in the sample.

8. Probes and Immunoassays

VEGF-E amino acid variant sequences and derivatives that are immunologically crossreactive with antibodies raised against native VEGF are useful in immunoassays for VEGF-E as standards, or, when labeled, as competitive reagents.

The full-length nucleotide sequence SEQ ID NO:1, or portions thereof, may be used as hybridization probes for a cDNA library to isolate the full-length VEGF-E gene or to isolate still other genes (for instance, those encoding naturally-occurring variants of VEGF-E or VEGF-E from other species) which have a desired sequence identity to the VEGF-E sequence disclosed in FIG. 1 (SEQ ID NO:1). Optionally, the length of the probes will be about 17 to about 50 bases. The hybridization probes may be derived from the nucleotide sequence of SEQ ID NO:1 as shown in FIG. 1 or from genomic sequences including promoters, enhancer elements, and introns of native-sequence VEGF-E-encoding DNA. By way of example, a screening method will comprise isolating the coding region of the VEGF-E gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the VEGF-E gene of the present invention can be used to screen libraries of human cDNA, genomic DNA, or mRNA to determine which members of such libraries the probe hybridizes to. Hybridization techniques are described in further detail in the Examples below.

The probes may also be employed in PCR techniques to generate a pool of sequences for identification of closely related VEGF-E sequences.

9. Chromosome Mapping

Nucleotide sequences encoding a VEGF-E polypeptide can also be used to construct hybridization probes for mapping the gene which encodes that VEGF-E polypeptide and for the genetic analysis of individuals with genetic disorders. The nucleotide sequence provided herein may be mapped to a chromosome and specific regions of a chromosome using known techniques, such as in situ hybridization, linkage analysis against known chromosomal markers, and hybridization screening with libraries.

For chromosome identification, the sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease. Briefly, sequences can be mapped to chromosomes by preparing PCR primers (preferably 15-25 bp) from the cDNA. Computer analysis for the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes, and preselection by hybridization to construct chromosome-specific cDNA libraries.

Fluorescence in situ hybridization (FISH) of a cDNA clone to a metaphase chromosomal spread can be used to provide a precise chromosomal location in one step. This technique can be used with DNA as short as 500 or 600 bases; however, clones larger than 2,000 bp have a higher likelihood of binding to a unique chromosomal location with sufficient signal intensity for simple detection. FISH requires use of the clones from which the gene encoding VEGF-E polypeptide was derived, and the longer the better. For example, 2,000 bp is good, 4,000 bp is better, and more than 4,000 is probably not necessary to get good results a reasonable percentage of the time. For a review of this technique, see Verma et al., *Human Chromosomes: a Manual of Basic Techniques* (Pergamon Press, New York, 1988).

Once a sequence has been mapped to a precise chromosomal location, the physical position of the sequence on the chromosome can be correlated with genetic map data. Such data are found, for example, in V. McKusick, *Mendelian Inheritance in Man* (available on line through Johns Hopkins University Welch Medical Library). The relationship between genes and diseases that have been mapped to the same chromosomal region is then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

10. Screening Assays for Drug Candidates

Screening assays can be designed to find lead compounds that mimic the biological activity of a native VEGF-E or a receptor for VEGF-E. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Hence, this invention encompasses methods of screening compounds to identify those that mimic the VEGF-E polypeptide (agonists) or prevent the effect of the VEGF-E polypeptide (antagonists). Screening assays for antagonist drug candidates are designed to identify compounds that bind or complex with the VEGF-E polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a VEGF-E polypeptide encoded by a nucleic acid identified herein under conditions and for a time sufficient to allow these two components to interact.

In binding assays, the interaction is binding and the complex formed can be isolated or detected in the reaction mixture. In a particular embodiment, the VEGF-E polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the VEGF-E polypeptide and drying. Alternatively, an immobilized antibody, e.g., a monoclonal antibody, specific for the VEGF-E polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular VEGF-E polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature* (*London*), 340: 245-246 (1989); Chien et al., *Proc. Natl. Acad. Sci. USA*, 88: 9578-9582 (1991)) as disclosed by Chevray and Nathans, *Proc. Natl. Acad. Sci. USA*, 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a VEGF-E polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

If the VEGF-E polypeptide has the ability to stimulate the proliferation of endothelial cells in the presence of the co-mitogen ConA, then one example of a screening method takes advantage of this ability. Specifically, in the proliferation assay, human umbilical vein endothelial cells are obtained and cultured in 96-well flat-bottomed culture plates (Costar, Cambridge, Mass.) and supplemented with a reaction mixture appropriate for facilitating proliferation of the cells, the mixture containing Con-A (Calbiochem, La Jolla, Calif.). Con-A and the compound to be screened are added and after incubation at 37° C., cultures are pulsed with $^3$-H-thymidine and harvested onto glass fiber filters (phD; Cambridge Technology, Watertown, Mass.). Mean $^3$-(H) thymidine incorporation (cpm) of triplicate cultures is determined using a liquid scintillation counter (Beckman Instruments, Irvine, Calif.). Significant $^3$-(H)thymidine incorporation indicates stimulation of endothelial cell proliferation.

To assay for antagonists, the assay described above is performed; however, in this assay the VEGF-E polypeptide is added along with the compound to be screened and the ability of the compound to inhibit $^3$-(H)thymidine incorporation in the presence of the VEGF-E polypeptide indicates that the compound is an antagonist to the VEGF-E polypeptide. Alternatively, antagonists may be detected by combining the VEGF-E polypeptide and a potential antagonist with membrane-bound VEGF-E polypeptide receptors or recombinant receptors under appropriate conditions for a competitive inhibition assay. The VEGF-E polypeptide can be labeled, such as by radioactivity, such that the number of VEGF-E polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.*, 1(2): Chapter 5 (1991). Preferably, expression cloning is employed wherein polyadenylated RNA is prepared from a cell responsive to the VEGF-E polypeptide and a cDNA library created from this RNA is divided into pools and used to transfect COS cells or other cells that are not responsive to the VEGF-E polypeptide. Transfected cells that are grown on glass slides are exposed to labeled VEGF-E polypeptide. The VEGF-E polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled VEGF-E polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled VEGF-E polypeptide in the presence of the candidate compound. The ability of the compound to enhance or block this interaction could then be measured. The compositions useful in the treatment of cardiovascular, endothelial, and angiogenic disorders include, without limitation, antibodies, small organic and inorganic molecules, peptides, phosphopeptides, antisense and ribozyme molecules, triple-helix molecules, etc., that inhibit the expression and/or activity of the target gene product.

More specific examples of potential antagonists include an oligonucleotide that binds to the VEGF-E polypeptide, (poly)peptide-immunoglobulin fusions, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the VEGF-E polypeptide that recognizes the receptor but imparts no effect, thereby competitively inhibiting the action of the VEGF-E polypeptide.

Another potential VEGF-E polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature VEGF-E polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6: 3073 (1979); Cooney at al., *Science*, 241: 456 (1988); Dervan et al., *Science*, 251: 1360 (1991)), thereby preventing transcription and the production of the VEGF-E polypeptide. The antisense RNA oligonucleotide hybridizes to the mRNA in viva and blocks translation of the mRNA molecule into the VEGF-E polypeptide (antisense—Okano, *Neurochem.*, 56: 560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in viva to inhibit production of the VEGF-E polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the VEGF-E polypeptide, thereby blocking the normal biological activity of the VEGF-E polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4: 469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

11. Types of Cardiovascular, Endothelial, and Angiogenic Disorders to be Treated The VEGF-E polypeptides, or agonists or antagonists thereto, that have activity in the cardiovascular, angiogenic, and endothelial assays described herein, and/or whose gene product has been found to be localized to the cardiovascular system, are likely to have therapeutic uses in a variety of cardiovascular, endothelial, and angiogenic disorders, including systemic disorders that affect vessels, such as diabetes mellitus. The VEGF-E molecules herein have a number of therapeutic uses associated with survival, proliferation and/or differenetion of cells. Such uses include the treatment of umbilical vein endothelial cells, in view of the demonstrated ability of VEGF-E to increase survival of human umbilical vein endothelial cells. Treatment may be needed if the vein were subjected to traumata, or situations wherein artificial means are employed to enhance the survival of the umbilical vein, for example, where it is weak, diseased, based on an artificial matrix, or in an artificial environment. Other physiological conditions that could be improved based on the selective mitogenic character of VEGF-E are also included herein. Uses also include the treatment of fibroblasts and myocytes, in view of the demonstrated ability of VEGF-E to induce proliferation of fibroblasts and hypertrophy in myocytes. In particular, VEGF-E can be used in wound healing, tissue growth and muscle generation and regeneration.

Their therapeutic utility could include diseases of the arteries, capillaries, veins, and/or lymphatics. Examples of treatments hereunder include treating muscle wasting disease, treating osteoporosis, aiding in implant fixation to stimulate the growth of cells around the implant and therefore facilitate its attachment to its intended site, increasing IGF stability in tissues or in serum, if applicable, and increasing binding to the IGF receptor (since IGF has been shown in vitro to enhance human marrow erythroid and granulocytic progenitor cell growth).

The VEGF-E polypeptides or agonists or antagonists thereto may also be employed to stimulate erythropoiesis or granulopoiesis, to stimulate wound healing or tissue regeneration and associated therapies concerned with re-growth of tissue, such as connective tissue, skin, bone, cartilage, muscle, lung, or kidney, to promote angiogenesis, to stimulate or inhibit migration of endothelial cells, and to proliferate the growth of vascular smooth muscle and endothelial cell production. The increase in angiogenesis mediated by VEGF-E polypeptide or antagonist would be beneficial to ischemic tissues and to collateral coronary development in the heart subsequent to coronary stencsis. Antagonists are used to inhibit the action of such polypeptides, for example, to limit the production of excess connective tissue during wound healing or pulmonary fibrosis if the VEGF-E polypeptide promotes such production. This would include treatment of acute myocardial infarction and heart failure.

Moreover, the present invention concerns the treatment of cardiac hypertrophy, regardless of the underlying cause, by administering a therapeutically effective dose of VEGF-E polypeptide, or agonist or antagonist thereto. If the objective is the treatment of human patients, the VEGF-E polypeptide preferably is recombinant human VEGF-E polypeptide (rh-VEGF-E polypeptide). The treatment for cardiac hypertrophy can be performed at any of its various stages, which may result from a variety of diverse pathologic conditions, including myocardial infarction, hypertension, hypertrophic cardiomyopathy, and valvular regurgitation. The treatment extends to all stages of the progression of cardiac hypertrophy, with or without structural damage of the heart muscle, regardless of the underlying cardiac disorder.

The decision of whether to use the molecule itself or an agonist thereof for any particular indication, as opposed to an antagonist to the molecule, would depend mainly on whether the molecule herein promotes cardiovascularization, genesis of endothelial cells, or angiogenesis or inhibits these conditions. For example, if the molecule promotes angiogenesis, an antagonist thereof would be useful for treatment of disorders where it is desired to limit or prevent angiogenesis. Examples of such disorders include vascular tumors such as haemangioma, tumor angiogenesis, neovascularization in the retina, choroid, or cornea, associated with diabetic retinopathy or premature infant retinopathy or macular degeneration and proliferative vitreoretinopathy, rheumatoid arthritis, Crohn's disease, atherosclerosis, ovarian hyperstimulation, psoriasis, endometriosis associated with neovascularization, restenosis subsequent to balloon angioplasty, scar tissue overproduction, for example, that seen in a keloid that forms after surgery, fibrosis after myocardial infarction, or fibrotic lesions associated with pulmonary fibrosis.

If, however, the molecule inhibits angiogenesis, it would be expected to be used directly for treatment of the above conditions.

On the other hand, if the molecule stimulates angiogenesis it would be used itself (or an agonist thereof) for indications where angiogenesis is desired such as peripheral vascular disease, hypertension, inflammatory vasculitides, Reynaud's disease and Reynaud's phenomenon, aneurysms, arterial restenosis, thrombophlebitis, lymphangitis, lymphedema, wound healing and tissue repair, ischemia reperfusion injury, angina, myocardial infarctions such as acute myocardial infarctions, chronic heart conditions, heart failure such as congestive heart failure, and osteoporosis. If, however, the molecule inhibits angiogenesis, an antagonist thereof would be used for treatment of those conditions where angiogenesis is desired.

Specific types of diseases are described below, where the VEGF-E polypeptide herein or antagonists thereof may serve as useful for vascular-related drug targeting or as therapeutic targets for the treatment or prevention of the disorders. Atherosclerosis is a disease characterized by accumulation of plaques of intimal thickening in arteries, due to accumulation of lipids, proliferation of smooth muscle cells, and formation of fibrous tissue within the arterial wall. The disease can affect large, medium, and small arteries in any organ. Changes in endothelial and vascular smooth muscle cell function are known to play an important role in modulating the accumulation and regression of these plaques.

Hypertension is characterized by raised vascular pressure in the systemic arterial, pulmonary arterial, or portal venous systems. Elevated pressure may result from or result in impaired endothelial function and/or vascular disease.

Inflammatory vasculitides include giant cell arteritis, Takayasu's arteritis, polyarteritis nodosa (including the microangiopathic form), Kawasaki's disease, microscopic polyangiitis, Wegener's granulomatosis, and a variety of infectious-related vascular disorders (including Henoch-Schonlein prupura). Altered endothelial cell function has been shown to be important in these diseases.

Reynaud's disease and Reynaud's phenomenon are characterized by intermittent abnormal impairment of the circulation through the extremities on exposure to cold. Altered endothelial cell function has been shown to be important in this disease.

Aneurysms are saccular or fusiform dilatations of the arterial or venous tree that are associated with altered endothelial cell and/or vascular smooth muscle cells.

Arterial restenosis (restenosis of the arterial wall) may occur following angioplasty as a result of alteration in the function and proliferation of endothelial and vascular smooth muscle cells.

Thrombophlebitis and lymphangitis are inflammatory disorders of veins and lymphatics, respectively, that may result from, and/or in, altered endothelial cell function. Similarly, lymphedema is a condition involving impaired lymphatic vessels resulting from endothelial cell function.

The family of benign and malignant vascular tumors are characterized by abnormal proliferation and growth of cellular elements of the vascular system.

For example, lymphangiomas are benign tumors of the lymphatic system that are congenital, often cystic, malformations of the lymphatics that usually occur in newborns. Cystic tumors tend to grow into the adjacent tissue. Cystic tumors usually occur in the cervical and axillary region. They can also occur in the soft tissue of the extremities. The main symptoms are dilated, sometimes reticular, structured lymphatics and lymphocysts surrounded by connective tissue. Lymphangiomas are assumed to be caused by improperly connected embryonic lymphatics or their deficiency. The result is impaired local lymph drainage. Griener et al., *Lymphology*, 4: 140-144 (1971).

Another use for the VEGF-E polypeptides herein or antagonists thereto is in the prevention of tumor angiogenesis, which involves vascularization of a tumor to enable it to growth and/or metastasize. This process is dependent on the growth of new blood vessels. Examples of neoplasms and related conditions that involve tumor angiogenesis include breast carcinomas, lung carcinomas, gastric carcinomas, esophageal carcinomas, colorectal carcinomas, liver carcinomas, ovarian carcinomas, thecomas, arrhenoblastomas, cervical carcinomas, endometrial carcinoma, endometrial hyperplasia, endometriosis, fibrosarcomas, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreas carcinomas, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as that associated with brain tumors), and Meigs' syndrome.

Age-related macular degeneration (AMD) is a leading cause of severe visual loss in the elderly population. The exudative form of AMD is characterized by choroidal neovascularization and retinal pigment epithelial cell detachment. Because choroidal neovascularization is associated with a dramatic worsening in prognosis, the VEGF-E polypeptides or antagonist thereto is expected to be useful in reducing the severity of AMD.

Healing of trauma such as wound healing and tissue repair is also a targeted use for the VEGF-E polypeptides herein or their antagonists. Formation and regression of new blood vessels is essential for tissue healing and repair. This category includes bone, cartilage, tendon, ligament, and/or nerve tissue growth or regeneration, as well as wound healing and tissue repair and replacement, and in the treatment of burns, incisions, and ulcers.

A VEGF-E polypeptide or antagonist thereof that induces cartilage and/or bone growth in circumstances where bone is not normally formed has application in the healing of bone fractures and cartilage damage or defects in humans and other animals. Such a preparation employing a VEGF-E polypeptide or antagonist thereof may have prophylactic use in closed as well as open fracture reduction and also in the improved fixation of artificial joints. De novo bone formation induced by an osteogenic agent contributes to the repair of congenital, trauma-induced, or oncologic, resection-induced craniofacial defects, and also is useful in cosmetic plastic surgery.

VEGF-E polypeptides or antagonists thereto may also be useful to promote better or faster closure of non-healing wounds, including without limitation pressure ulcers, ulcers associated with vascular insufficiency, surgical and traumatic wounds, and the like.

It is expected that a VEGF-E polypeptide or antagonist thereto may also exhibit activity for generation or regeneration of other tissues, such as organs (including, for example, pancreas, liver, intestine, kidney, skin, or endothelium), muscle (smooth, skeletal, or cardiac), and vascular (including vascular endothelium) tissue, or for promoting the growth of cells comprising such tissues. Part of the desired effects may be by inhibition or modulation of fibrotic scarring to allow normal tissue to regenerate.

A VEGF-E polypeptide herein or antagonist thereto may also be useful for gut protection or regeneration and treatment of lung or liver fibrosis, reperfusion injury in various tissues, and conditions resulting from systemic cytokine damage. Also, the VEGF-E polypeptide or antagonist thereto may be useful for promoting or inhibiting differentiation of tissues described above from precursor tissues or cells, or for inhibiting the growth of tissues described above.

A VEGF-E polypeptide or antagonist thereto may also be used in the treatment of periodontal diseases and in other tooth-repair processes. Such agents may provide an environment to attract bone-forming cells, stimulate growth of bone-forming cells, or induce differentiation of progenitors of bone-forming cells. A VEGF-E polypeptide herein or an antagonist thereto may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes, since blood vessels play an important role in the regulation of bone turnover and growth.

Another category of tissue regeneration activity that may be attributable to the VEGF-E polypeptide herein or antagonist thereto is tendon/ligament formation. A protein that induces tendon/ligament-like tissue or other tissue formation in circumstances where such tissue is not normally formed has application in the healing of tendon or ligament tears, deformities, and other tendon or ligament defects in humans and other animals. Such a preparation may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the VEGF-E polypeptide herein or antagonist thereto contributes to the repair of congenital, trauma-induced, or other tendon or ligament defects of other origin, and is also useful in cosmetic plastic surgery for attachment or repair of tendons or ligaments. The compositions herein may provide an environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions herein may also be useful in the treatment of tendinitis, carpal tunnel syndrome, and other tendon or ligament defects. The compositions may also include an appropriate matrix and/or sequestering agent as a carrier as is well known in the art.

The VEGF-E polypeptide or its antagonist may also be useful for proliferation of neural cells and for regeneration of nerve and brain tissue, i.e., for the treatment of central and peripheral nervous system disease and neuropathies, as well as mechanical and traumatic disorders, that involve degeneration, death, or trauma to neural cells or nerve tissue. More specifically, a VEGF-E polypeptide or its antagonist may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions that may be treated in accordance with the present invention include mechanical and traumatic disorders, such as spinal cord disorders, head trauma, and cerebrovascular diseases such as stroke. Peripheral neuropathies resulting from chemotherapy or other medical therapies may also be treatable using a VEGF-E polypeptide herein or antagonist thereto.

Ischemia-reperfusion injury is another indication. Endothelial cell dysfunction may be important in both the initiation of, and in regulation of the sequelae of events that occur following ischemia-reperfusion injury.

Rheumatoid arthritis is a further indication. Blood vessel growth and targeting of inflammatory cells through the vasculature is an important component in the pathogenesis of rheumatoid and sero-negative forms of arthritis. VEGF-E polypeptide or its antagonist may also be administered prophylactically to patients with cardiac hypertrophy, to prevent the progression of the condition, and avoid sudden death, including death of asymptomatic patients. Such preventative therapy is particularly warranted in the case of patients diagnosed with massive left ventricular cardiac hypertrophy (a maximal wall thickness of 35 mm or more in adults, or a comparable value in children), or in instances when the hemodynamic burden on the heart is particularly strong.

VEGF-E polypeptide or its antagonist may also be useful in the management of atrial fibrillation, which develops in a substantial portion of patients diagnosed with hypertrophic cardiomyopathy.

Further indications include angina, myocardial infarctions such as acute myocardial infarctions, and heart failure such as congestive heart failure. Additional non-neoplastic conditions include psoriasis, diabetic and other proliferative retinopathies including retinopathy of prematurity, retrolental fibroplasia, neovascular glaucoma, thyroid hyperplasias (including Grave's disease), corneal and other tissue transplantation, chronic inflammation, lung inflammation, nephrotic syndrome, preeclampsia, ascites, pericardial effusion (such as that associated with pericarditis), and pleural effusion.

In view of the above, the VEGF-E polypeptides or agonists or antagonists thereof described herein, which are shown to alter or impact endothelial cell function, proliferation, and/or form, are likely to play an important role in the etiology and pathogenesis of many or all of the disorders noted above, and as such can serve as therapeutic targets to augment or inhibit these processes or for vascular-related drug targeting in these disorders.

12. Administration Protocols, Schedules, Doses, and Formulations

The molecules herein and agonists and antagonists thereto are pharmaceutically useful as a prophylactic and therapeutic agent for various disorders and diseases as set forth above.

The VEGF-E of the present invention can be formulated according to known methods to prepare pharmaceutically-useful compositions, whereby the VEGF-E hereof is combined in admixture with a pharmaceutically acceptable carrier vehicle. Suitable carrier vehicles and their formulation, inclusive of other human proteins, e.g., human serum albumin, are described, for example, in Remington's *Pharmaceutical Sciences*, 16th ed., 1980, Mack Publishing Co., edited by Oslo et al. The VEGF-E herein may be administered parenterally to subjects suffering from cardiovascular diseases or conditions, or by other methods that ensure its delivery to the bloodstream in an effective form.

Compositions particularly well suited for the clinical administration of VEGF-E hereof employed in the practice of the present invention include, for example, sterile aqueous solutions, or sterile hydratable powders such as lyophilized protein. It is generally desirable to include further in the formulation an appropriate amount of a pharmaceutically acceptable salt, generally in an amount sufficient to render the formulation isotonic. A pH regulator such as arginine base, and phosphoric acid, are also typically included in sufficient quantities to maintain an appropriate pH, generally from 5.5 to 7.5. Moreover, for improvement of shelf-life or stability of aqueous formulations, it may also be desirable to include further agents such as glycerol. In this manner, variant VEGF-E formulations are rendered appropriate for parenteral administration, and, in particular, intravenous administration.

Therapeutic compositions of the VEGF-E polypeptides or agonists or antagonists are prepared for storage by mixing the desired molecule having the appropriate degree of purity with optional pharmaceutically acceptable carriers, excipients, or stabilizers (*Remington's Pharmaceutical Sciences*, 16th edition, Oslo, A. ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Additional examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of antagonist include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations. The VEGF-E polypeptides or agonists or antagonists will typically be formulated in such vehicles at a concentration of about 0.1 mg/ml to 100 mg/ml.

Another formulation comprises incorporating a VEGF-E polypeptide or antagonist thereof into formed articles. Such articles can be used in modulating endothelial cell growth and angiogenesis. In addition, tumor invasion and metastasis may be modulated with these articles.

The VEGF-E to be used for therapeutic administration must be sterile. Sterility is readily accomplished by filtration through sterile filtration membranes (e.g., 0.2 micron membranes). The VEGF-E ordinarily will be stored in lyophilized form or as an aqueous solution if it is highly stable to thermal and oxidative denaturation. The pH of the VEGF-E preparations typically will be about from 6 to 8, although higher or lower pH values may also be appropriate in certain instances. It will be understood that use of certain of the foregoing excipients, carriers, or stabilizers will result in the formation of salts of the VEGF-E.

An isotonifier may be present to ensure isotonicity of a liquid composition of the VEGF-E polypeptide or antagonist thereto, and includes polyhydric sugar alcohols, preferably trihydric or higher sugar alcohols, such as glycerin, erythritol, arabitol, xylitol, sorbitol, and mannitol. These sugar alcohols can be used alone or in combination. Alternatively, sodium chloride or other appropriate inorganic salts may be used to render the solutions isotonic.

The buffer may, for example, be an acetate, citrate, succinate, or phosphate buffer depending on the pH desired. The pH of one type of liquid formulation of this invention is buffered in the range of about 4 to 8, preferably about physiological pH.

The preservatives phenol, benzyl alcohol and benzethonium halides, e.g., chloride, are known antimicrobial agents that may be employed.

Therapeutic VEGF-E polypeptide compositions generally are placed into a container having a sterile access port, for example, an intravenous solution bag or vial having a stopper pierceable by a hypodermic injection needle. The formulations are preferably administered as repeated intravenous (i.v.), subcutaneous (s.c.), or intramuscular (i.m.) injections, or as aerosol formulations suitable for intranasal or intrapulmonary delivery (for intrapulmonary delivery see, e.g., EP 257,956).

VEGF-E polypeptide can also be administered in the form of sustained-released preparations. Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res*., 15: 167-277 (1981) and Langer, *Chem. Tech*., 12: 98-105 (1982) or poly(vinylalcohol)), polylactides (U.S. Pat. No. 3,773,919, EP 58,481), copolymers of L-glutamic acid and gamma ethyl-L-glutamate (Sidman et al., *Biopolymers*, 22: 547-556 (1983)), non-degradable ethylene-vinyl acetate (Langer et al., supra), degradable lactic acid-glycolic acid copolymers such as the Lupron Depot☐ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions. Sustained-release VEGF-E polypeptide compositions also include liposomally entrapped VEGF-E polypeptide. Liposomes containing VEGF-E polypeptide are prepared by methods known per se: DE 3,218,121; Epstein et al., *Proc. Natl. Acad. Sci. USA*, 82: 3688-3692 (1985); Hwang et al., *Proc. Natl. Acad. Sci. USA*, 77: 4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamellar type in which the lipid content is greater than about 30 mol. % cholesterol, the selected proportion being adjusted for the optimal therapy.

The therapeutically effective dose of VEGF-E polypeptide or antagonist thereto will, of course, vary depending on such factors as the pathological condition to be treated (including prevention), the method of administration, the type of compound being used for treatment, any co-therapy involved, the patient's age, weight, general medical condition, medical history, etc., and its determination is well within the skill of a practicing physician. Accordingly, it will be necessary for the therapist to titer the dosage and modify the route of administration as required to obtain the maximal therapeutic effect. If the VEGF-E polypeptide has a narrow host range, for the treatment of human patients formulations comprising human VEGF-E polypeptide, more preferably native-sequence human VEGF-E polypeptide, are preferred. The clinician will administer VEGF-E polypeptide until a dosage is reached that achieves the desired effect for treatment of the condition in question. For example, if the objective is the treatment of CHF, the amount would be one that inhibits the progressive cardiac hypertrophy associated with this condition. The progress of this therapy is easily monitored by echo cardiography. Similarly, in patients with hypertrophic cardiomyopathy, VEGF-E polypeptide can be administered on an empirical basis.

With the above guidelines, the effective dose generally is within the range of from about 0.001 to about 1.0 mg/kg, more preferably about 0.01-1 mg/kg, most preferably about 0.01-0.1 mg/kg.

For non-oral use in treating human adult hypertension, it is advantageous to administer VEGF-E polypeptide in the form of an injection at about 0.01 to 50 mg, preferably about 0.05 to 20 mg, most preferably 1 to 20 mg, per kg body weight, 1 to 3 times daily by intravenous injection. For oral administration, a molecule based on the VEGF-E polypeptide is preferably administered at about 5 mg to 1 g, preferably about 10 to 100 mg, per kg body weight, 1 to 3 times daily. It should be appreciated that endotoxin contamination should be kept minimally at a safe level, for example, less than 0.5 ng/mg protein. Moreover, for human administration, the formulations preferably meet sterility, pyrogenicity, general safety, and purity as required by FDA Office and Biologics standards.

The dosage regimen of a pharmaceutical composition containing VEGF-E polypeptide to be used in tissue regeneration will be determined by the attending physician considering various, factors that modify the action of the polypeptides, e.g., amount of tissue weight desired to be formed, the site of damage, the condition of the damaged tissue, the size of a wound, type of damaged tissue (e.g., bone), the patient's age, sex, and diet, the severity of any infection, time of administration, and other clinical factors. The dosage may vary with the type of matrix used in the reconstitution and with inclusion of other proteins in the pharmaceutical composition. For example, the addition of other known growth factors, such as IGF-I, to the final composition may also affect the dosage. Progress can be monitored by periodic assessment of tissue/bone growth and/or repair, for example, X-rays, histomorphometric determinations, and tetracycline labeling.

The route of VEGF-E polypeptide or antagonist or agonist administration is in accord with known methods, e.g., by injection or infusion by intravenous, intramuscular, intracerebral, intraperitoneal, intracerobrospinal, subcutaneous, intraocular, intraarticular, intrasynovial, intrathecal, oral, topical, or inhalation routes, or by sustained-release systems as noted below. The VEGF-E polypeptide or antagonists thereof also are suitably administered by intratumoral, peritumoral, intralesional, or perilesional routes, to exert local as well as systemic therapeutic effects. The intraperitoneal route is expected to be particularly useful, for example, in the treatment of ovarian tumors.

If a peptide or small molecule is employed as an antagonist or agonist, it is preferably administered orally or non-orally in the form of a liquid or solid to mammals.

Examples of pharmacologically acceptable salts of molecules that form salts and are useful hereunder include alkali metal salts (e.g., sodium salt, potassium salt), alkaline earth metal salts (e.g., calcium salt, magnesium salt), ammonium salts, organic base salts (e.g., pyridine salt, triethylamine salt), inorganic acid salts (e.g., hydrochloride, sulfate, nitrate), and salts of organic acid (e.g., acetate, oxalate, p-toluenesulfonate).

For compositions herein that are useful for bone, cartilage, tendon, or ligament regeneration, the therapeutic method includes administering the composition topically, systemically, or locally as an implant or device. When administered, the therapeutic composition for use is in a pyrogen-free, physiologically acceptable form. Further, the composition may desirably be encapsulated or injected in a viscous form for delivery to the site of bone, cartilage, or tissue damage. Topical administration may be suitable for wound healing and tissue repair. Preferably, for bone and/or cartilage formation, the composition would include a matrix capable of delivering the protein-containing composition to the site of bone and/or cartilage damage, providing a structure for the developing bone and cartilage and preferably capable of being resorbed into the body. Such matrices may be formed of materials presently in use for other implanted medical applications.

The choice of matrix material is based on biocompatibility, biodegradabiity, mechanical properties, cosmetic appearance, and interface properties. The particular application of the compositions will define the appropriate formulation. Potential matrices for the compositions may be biodegradable and chemically defined calcium sulfate, tricalcium phosphate, hydroxyapatite, polylactic acid, polyglycolic acid, and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above-mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

One specific embodiment is a 50:50 (mole weight) copolymer of lactic acid and glycolic acid in the form of porous particles having diameters ranging from 150 to 800 microns. in some applications, it will be useful to utilize a sequestering agent, such as carboxymethyl cellulose or autologous blood clot, to prevent the polypeptide compositions from disassociating from the matrix.

One suitable family of sequestering agents is cellulosic materials such as alkylcelluloses (including hydroxyalkylcelluloses), including methylcellulose, ethylcellulose, hydoxyethylcellulose, hydroxypropylcellulose, hydroxypropylmethylcellulose, and carboxymethylcellulose, one preferred being cationic salts of carboxymethylcellulose (CMC). Other preferred sequestering agents include hyaluronic acid, sodium alginate, poly(ethylene glycol), polyoxyethylene oxide, carboxyvinyl polymer, and poly(vinyl alcohol). The amount of sequestering agent useful herein is 0.5-20 wt %, preferably 1-10 wt %, based on total formulation weight, which represents the amount necessary to prevent desorption of the polypeptide (or its antagonist) from the polymer matrix and to provide appropriate handling of the composition, yet not so much that the progenitor cells are prevented from infiltrating the matrix, thereby providing the polypeptide (or its antagonist) the opportunity to assist the osteogenic activity of the progenitor cells.

Generally, where the disorder permits, one should formulate and dose the VEGF-E for site-specific delivery. This is convenient in the case of wounds and ulcers.

When applied topically, the VEGF-E is suitably combined with other ingredients, such as carriers and/or adjuvants. There are no limitations on the nature of such other ingredients, except that they must be pharmaceutically acceptable and efficacious for their intended administration, and cannot degrade the activity of the active ingredients of the composition.

Examples of suitable vehicles include ointments, creams, gels, or suspensions, with or without purified collagen. The compositions also may be impregnated into transdermal patches, plasters, and bandages, preferably in liquid or semi-liquid form. For obtaining a gel formulation, the VEGF-E formulated in a liquid composition may be mixed with an effective amount of a water-soluble polysaccharide or synthetic polymer such as polyethylene glycol to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans;—arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the VEGF-E held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low- and high-molecular-weight polyethylene glycols to obtain the proper viscosity. For example, a mixture of a polyethylene glycol of molecular weight 400-600 with one of molecular weight 1500 would be effective for this purpose when mixed in the proper ratio to obtain a paste.

The term “water soluble” as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2-5%, more preferably about 3%, of the gel and the VEGF-E is present in an amount of about 300-1000 mg per ml of gel.

13. Combination Therapies

The effectiveness of the VEGF-E polypeptide or an agonist or antagonist thereof in preventing or treating the disorder in question may be improved by administering the active agent serially or in combination with another agent that is effective for those purposes, either in the same composition or as separate compositions. Hence, it is within the scope hereof to combine the VEGF-E therapy with other novel or conventional therapies (e.g., growth factors such as VEGF, aFGF, bFGF, PDGF, IGF, NGF, anabolic steroids, EGF or TGF-alpha) for enhancing the activity of any of the growth factors, including VEGF-E, in promoting cell proliferation, survival, differentiation, and repair. It is not necessary that such cotreatment drugs be included per se in the compositions of this invention, although this will be convenient where such drugs are proteinaceous. Such admixtures are suitably administered in the same manner and for the same purposes as the VEGF-E used alone.

For treatment of cardiac hypertrophy, VEGF-E polypeptide therapy can be combined with the administration of inhibitors of known cardiac myocyte hypertrophy factors, e.g., inhibitors of α-adrenergic agonists such as phenylephrine; endothelin-1 inhibitors such as BOSENTAN™ and MOXONODIN™; inhibitors to CT-1 (US Pat. No. 5,679, 545); inhibitors to LIF; ACE inhibitors; des-aspartate-angiotensin I inhibitors (U.S. Pat. No. 5,773,415), and angiotensin II inhibitors.

For treatment of cardiac hypertrophy associated with hypertension, VEGF-E polypeptide can be administered in combination with β-adrenergic receptor blocking agents, e.g., propranolol, timolol, tertalolol, carteolol, nadolol, betaxolol, penbutolol, acetobutolol, atenolol, metoprolol, or carvedilol; ACE inhibitors, e.g., quinapril, captopril, enalapril, ramipril, benazepril, fosinopril, or lisinopril; diuretics, e.g., chorothiazide, hydrochlorothiazide, hydroflumethazide, methylchlothiazide, benzthiazide, dichlorphenamide, acetazolamide, or indapamide; and/or calcium channel blockers, e.g., diltiazem, nifedipine, verapamil, or nicardipine. Pharmaceutical compositions comprising the therapeutic agents identified herein by their generic VEGF-Es are commercially available, and are to be administered following the manufacturersU instructions for dosage, administration, adverse effects, contraindications, etc. See, e.g., *Physicians[] Desk Reference* (Medical Economics Data Production Co.: Montvale, N.J., 1997), 51th Edition.

Preferred candidates for combination therapy in the treatment of hypertrophic cardiomyopathy are β-adrenergic-blocking drugs (e.g., propranolol, timolol, tertalolol, carteolol, nadolol, betaxolol, penbutolol, acetobutolol, atenolol, metoprolol, or carvedilol), verapamil, difedipine, or diltiazem. Treatment of hypertrophy associated with high blood pressure may require the use of antihypertensive drug therapy, using calcium channel blockers, e.g., diltiazem, nifedipine, verapamil, or nicardipine; β-adrenergic blocking agents; diuretics, e.g., chorothiazide, hydrochlorothiazide, hydroflumethazide, methylchlothiazide, benzthiazide, dichlorphenamide, acetazolamide, or indapamide; and/or ACE-inhibitors, e.g., quinapril, captopril, enalapril, ramipril, benazepril, fosinopril, or lisinopril.

For other indications, VEGF-E polypeptides or their antagonists may be combined with other agents beneficial to the treatment of the bone and/or cartilage defect, wound, or tissue in question. These agents include various growth factors such as EGF, PDGF, TGF-α or TGF-β, IGF, FGF, and CTGF.

In addition, VEGF-E polypeptides or their antagonists used to treat cancer may be combined with cytotoxic, chemotherapeutic, or growth-inhibitory agents as identified above. Also, for cancer treatment, the VEGF-E polypeptide or antagonist thereof is suitably administered serially or in combination with radiological treatments, whether involving irradiation or administration of radioactive substances.

The effective amounts of the therapeutic agents administered in combination with VEGF-E polypeptide or antagonist thereof will be at the physician[]s or veterinarian[]s discretion. Dosage administration and adjustment is done to achieve maximal management of the conditions to be treated. For example, for treating hypertension, these amounts ideally take into account use of diuretics or digitalis, and conditions such as hyper- or hypotension, renal impairment, etc. The dose will additionally depend on such factors as the type of the therapeutic agent to be used and the specific patient being treated. Typically, the amount employed will be the same dose as that used, if the given therapeutic agent is administered without VEGF-E polypeptide. A useful molar ratio of VEGF-E to secondary growth factors is typically 1:0.1-10, with about equimolar amounts being preferred.

14. Articles of Manufacture

An article of manufacture such as a kit containing VEGF-E polypeptide or antagonists thereof useful for the diagnosis or treatment of the disorders described above comprises at least a container and a label. Suitable containers include, for example, bottles, vials, syringes, and test tubes. The containers may be formed from a variety of materials such as glass or plastic. The container holds a composition that is effective for diagnosing or treating the condition and may have a sterile access port (for example, the container may be an intravenous solution bag or a vial having a stopper pierceable by a hypodermic injection needle). The active agent in the composition is the VEGF-E polypeptide or an agonist or antagonist thereto. The label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use. The article of manufacture may also comprise a second or third container with another active agent as described above.

F. Anti-VEGF-E Antibodies

The present invention further provides anti-VEGF-E polypeptide antibodies. Exemplary antibodies include polyclonal, monoclonal, humanized, bispecific, and heteroconjugate antibodies.

1. Polyclonal Antibodies

The anti-VEGF-E antibodies of the present invention may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the VEGF-E polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-VEGF-E antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the VEGF-E polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high-level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, *J. Immunol.*, 133:3001 (1984); Brodeur et ail., *Monoclonal Antibody Production Techniques and Applications*, Marcel Dekker, Inc., New York, (1987) pp. 51-63).

The culture medium in which the hybridoma cells are cultured can then be assayed for the presence of monoclonal antibodies directed against a VEGF-E polypeptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy- and light-chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using routine techniques known in the art.

3. Humanized Antibodies

The anti-VEGF-E antibodies of the invention may further comprise humanized antibodies or human antibodies. Humanized forms of non-human (e.g., murine) antibodies are chimeric immunoglobulins, immunoglobulin chains, or fragments thereof (such as Fv, Fab, Fab', $F(ab')_2$, or other antigen-binding subsequences of antibodies) which contain minimal sequence derived from non-human immunoglobulin. Humanized antibodies include human immunoglobulins (recipient antibody) in which residues from a complementary-determining region (CDR) of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., *Nature*, 321:522-525 (1986); Riechmann et al., *Nature*, 332:323-329 (1988); and Presta, *Curr. Op. Struct. Biol*., 2:593-596 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom and Winter, *J. Mol. Biol.*, 227:381 (1991); Marks et al., *J. Mol. Biol.*, 222:581 (1991)). The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., J. Immunol., 147(1):86-95 (1991)).

4. Bispecific Antibodies

Bispecific antibodies are monoclonal, preferably human or humanized, antibodies that have binding specificities for at least two different antigens. In the present case, one of the binding specificities is for a VEGF-E polypeptide, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, *Nature*, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.*, 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176: 1191-1195 (1992) and Shopes, *J. Immunol.*, 148: 2918-2922 (1992). Homodimeric antibodies with enhanced anti-tumor activity may also be prepared using heterobifunctional cross-linkers as described in Wolff et al. *Cancer Research*, 53: 2560-2565 (1993). Alternatively, an antibody can be engineered that has dual Fc regions and may thereby have enhanced complement lysis and ADCC capabilities. See Stevenson et al., *Anti-Cancer Drug Design* 3: 219-230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radio-nuclides are available for the production of radioconjugated antibodies. Examples include $^{212}$Bi, $^{113}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14- labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., *Proc. Natl. Acad. Sci. USA*, 82: 3688 (1985); Hwang et al., *Proc. Natl Acad. Sci. USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem*. 257: 286-288 (1982) via a disulfide-interchange reaction. A chemotherapeutic agent (such as Doxorubicin) is optionally contained within the liposome. See Gabizon et al., *J. National Cancer Inst*. 81(19): 1484 (1989).

G. Uses for Anti-VEGF-E Antibodies

The anti-VEGF-E antibodies of the present invention have various utilities. For example, anti-VEGF-E antibodies may be used in diagnostic assays for VEGF-E polypeptides, e.g., detecting expression in specific cells, tissues, or serum. Various diagnostic assay techniques known in the art may be used, such as competitive binding assays, direct or indirect sandwich assays and immunoprecipitation assays conducted in either heterogeneous or homogeneous phases (Zola, *Monoclonal Antibodies: A Manual of Techniques*, CRC Press, Inc. (1987) pp. 147-158). The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-VEGF-E antibodies also are useful for the affinity purification of VEGF-E polypeptides from recombinant cell culture or natural sources. In this process, the antibodies against a VEGF-E polypeptide are immobilized on a suitable support, such as Sephadex™ resin or filter paper, using methods well known in the art. The immobilized antibody then is contacted with a sample containing the VEGF-E polypeptide to be purified, and thereafter the support is washed with a suitable solvent that will remove substantially all the material in the sample except the VEGF-E polypeptide, which is bound to the immobilized antibody. Finally, the support is washed with another suitable solvent that will release the VEGF-E polypeptide from the antibody.

1. Pharmaceutical Compositions of Antibodies

Antibodies specifically binding a VEGF-E polypeptide identified herein, as well as other molecules identified by the screening assays disclosed hereinbefore, can be administered for the treatment of various disorders as noted above and below in the form of pharmaceutical compositions.

If the VEGF-E polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA*, 90: 7889-7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

2. Methods of Treatment Using the Antibody

It is contemplated that the antibodies to VEGF-E polypeptide may be used to treat various cardiovascular, endothelial, and angiogenic conditions as noted above.

The antibodies are administered to a mammal, preferably a human, in accord with known methods, such as intravenous administration as a bolus or by continuous infusion over a period of time, by intramuscular, intraperitoneal, intracerebrospinal, subcutaneous, intra-articular, intrasynovial, intrathecal, oral, topical, or inhalation routes. Intravenous administration of the antibody is preferred.

Other therapeutic regimens may be combined with the administration of the antibodies of the instant invention as noted above. For example, if the antibodies are to treat cancer, the patient to be treated with such antibodies may also receive radiation therapy. Alternatively, or in addition, a chemotherapeutic agent may be administered to the patient. Preparation and dosing schedules for such chemotherapeutic agents may be used according to manufacturers' instructions or as determined empirically by the skilled practitioner. Preparation and dosing schedules for such chemotherapy are also described in *Chemotherapy Service*, Ed., M. C. Perry (Williams & Wilkins: Baltimore, Md., 1992). The chemotherapeutic agent may precede, or follow administration of the antibody, or may be given simultaneously therewith. The antibody may be combined with an anti-oestrogen compound such as tamoxifen or EVISTA™ or an anti-progesterone such as onapristone (see, EP 616812) in dosages known for such molecules.

If the antibodies are used for treating cancer, it may be desirable also to administer antibodies against other tumor-associated antigens, such as antibodies that bind to one or more of the ErbB2, EGFR, ErbB3, ErbB4, or VEGF receptor(s). These also include the agents set forth above. Also, the antibody is suitably administered serially or in combination with radiological treatments, whether involving irradiation or administration of radioactive substances. Alternatively, or in addition, two or more antibodies binding the same or two or more different antigens disclosed herein may be co-administered to the patient. Sometimes, it may be beneficial also to administer one or more cytokines to the patient. In a preferred embodiment, the antibodies herein are co-administered with a growth-inhibitory agent. For example, the growth-inhibitory agent may be administered first, followed by an antibody of the present invention. However, simultaneous administration or administration of the antibody of the present invention first is also contemplated. Suitable dosages for the growth-inhibitory agent are those presently used and may be lowered due to the combined action (synergy) of the growth-inhibitory agent and the antibody herein.

In one embodiment, vascularization of tumors is attacked in combination therapy. The anti-VEGF-E polypeptide and another antibody (e.g., anti-VEGF) are administered to tumor-bearing patients at therapeutically effective doses as determined, for example, by observing necrosis of the tumor or its metastatic foci, if any. This therapy is continued until such time as no further beneficial effect is observed or clinical examination shows no trace of the tumor or any metastatic foci. Then TNF is administered, alone or in combination with an auxiliary agent such as alpha-, beta-, or gamma-interferon, anti-HER2 antibody, heregulin, anti-heregulin antibody, D-factor, interleukin-1 (IL-1), interleukin-2 (IL-2), granulocyte-macrophage colony stimulating factor (GM-CSF), or agents that promote microvascular coagulation in tumors, such as anti-protein C antibody, anti-protein S antibody, or C4b binding protein (see WO 91/01753, published Feb. 21, 1991), or heat or radiation.

Since the auxiliary agents will vary in their effectiveness, it is desirable to compare their impact on the tumor by matrix screening in conventional fashion. The administration of anti-VEGF-E polypeptide antibody and TNF is repeated until the desired clinical effect is achieved. Alternatively, the anti-VEGF-E polypeptide antibody is administered together with TNF and, optionally, auxiliary agent(s). In instances where solid tumors are found in the limbs or in other locations susceptible to isolation from the general circulation, the therapeutic agents described herein are administered to the isolated tumor or organ. In other embodiments, a FGF or PDGF antagonist, such as an anti-FGF or an anti-PDGF neutralizing antibody, is administered to the patient in conjunction with the anti-VEGF-E polypeptide antibody. Treatment with anti-VEGF-E polypeptide antibodies preferably may be suspended during periods of wound healing or desirable neovascularization.

For the prevention or treatment of cardiovascular, endothelial, and angiogenic disorder, the appropriate dosage of an antibody herein will depend on the type of disorder to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

For example, depending on the type and severity of the disorder, about 1 µg/kg to 50 mg/kg (e.g., 0.1-20 mg/kg) of antibody is an initial candidate dosage for administration to the patient, whether, for example, by one or more separate administrations, or by continuous infusion. A typical daily or weekly dosage might range from about 1 µg/kg to 100 mg/kg or more, depending on the factors mentioned above. For repeated administrations over several days or longer, depending on the condition, the treatment is repeated or sustained until a desired suppression of disorder symptoms occurs. However, other dosage regimens may be useful. The progress of this therapy is easily monitored by conventional techniques and assays, including, for example, radiographic tumor imaging.

3. Articles of Manufacture with Antibodies

An article of manufacture containing a container with the antibody and a label is also provided. Such articles are described above, wherein the active agent is an anti-VEGF-E antibody.

4. Diagnosis and Prognosis of Tumors Using Antibodies

If the indication for which the antibodies are used is cancer, while cell-surface proteins, such as growth receptors overexpressed in certain tumors, are excellent targets for drug candidates or tumor (e.g., cancer) treatment, the same proteins along with VEGF-E polypeptides find additional use in the diagnosis and prognosis of tumors. For example, antibodies directed against the VEGF-E polypeptides may be used as tumor diagnostics or prognostics.

For example, antibodies, including antibody fragments, can be used qualitatively or quantitatively to detect the expression of genes including the gene encoding the VEGF-E polypeptide. The antibody preferably is equipped with a detectable, e.g., fluorescent label, and binding can be monitored by light microscopy, flow cytometry, fluorimetry, or other techniques known in the art. Such binding assays are performed essentially as described above.

In situ detection of antibody binding to the marker gene products can be performed, for example, by immunofluorescence or immunoelectron microscopy. For this purpose, a histological specimen is removed from the patient, and a labeled antibody is applied to it, preferably by overlaying the antibody on a biological sample. This procedure also allows for determining the distribution of the marker gene product in the tissue examined. It will be apparent to those skilled in the art that a wide variety of histological methods are readily available for in situ detection.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example I

Identification of Clones Encoding a VEGF-related Protein (VEGF-E)

Probes based on an expressed sequence tag (EST) identified from the Incyte Pharmaceuticals database due to homology with VEGF were used to screen a cDNA library derived from the human glioma cell line G61. In particular, Incyte Clone ⬛INC1302516" was used to generate the following four probes:

```
                                        (SEQ ID NO:3)
5'-ACTTCTCAGTGTCCATAAGGG;

(SEQ ID NO:4)
5'-GAACTAAAGAGAACCGATACCATTTTCTGGCCAGGTTGTC;

(SEQ ID NO:5)
5'-CACCACAGCGTTTAACCAGG;  and (SEQ ID NO:6)
5'-ACAACAGGCACAGTTCCCAC.
```

Nine positives were identified and characterized. Three clones contained the full coding region and were identical in sequence. Partial clones were also identified from a fetal lung library and were identical with the glioma-derived sequence with the exception of one nucleotide change, which did not alter the encoded amino acid.

Example 2

Expression Constructs

For mammalian protein expression, the entire open reading frame (ORF) was cloned into a CMV-based expression vector. An epitope-tag (FLAG™, Kodak) and Histidine-tag (His8) were inserted between the ORF and stop codon. VEGF-E-His8 and VEGF-E-FLAG were transfected into human embryonic kidney 293 cells by SuperFect™ (Qiagen) and pulse-labeled for 3 hours with ($^{35}$S)methionine and ($^{35}$C) cysteine. Both epitope-tagged proteins co-migrate when 20 microliters of 15-fold concentrated serum-free conditioned medium were electrophoresed on a polyacrylamide gel (Novex) in sodium dodecyl sulfate sample buffer (SDS-PAGE). The VEGF-E-IgG expression plasmid was constructed by cloning the ORF in front of the human Fc (IgG) sequence.

The VEGF-E-IgG plasmid was co-transfected with Baculogold Baculovirus™ DNA (Pharmingen) using Lipofectin™ (GibcoBRL) into $10^5$ Sf9 cells grown in Hink's™ TNM-FH medium (JRH Biosciences) supplemented with 10% fetal bovine serum. Cells were incubated for 5 days at 28° C. The supernatant was harvested and subsequently used for the first viral amplification by infecting Sf9 cells at an approximate multiplicity of infection (MOI) of 10. Cells were incubated for 3 days, then supernatant was harvested, and expression of the recombinant plasmid was determined by binding of 1 ml of supernatant to 30 µl of Protein-A Sepharose™ CL-4B beads (Pharmacia) followed by subsequent SDS-PAGE analysis. The first amplification supernatant was used to infect a 500 ml spinner culture of Sf9 cells grown in ESF-921 medium (Expression Systems LLC) at an approximate MOI of 0.1. Cells were treated as above, except harvested supernatant was sterile filtered. Specific protein was 26=purified by binding to Protein-A Sepharose 4 Fast Flow™ (Pharmacia) column.

Example 3

Northern Blot Analyses

Blots of human poly(A)+RNA from multiple adult and fetal tissues and tumor cell lines were obtained from Clontech (Palo Alto, Calif.). Hybridization was carried out using $^{32}$P-labeled probes containing the entire coding region and washed in 0.1×SSC, 0.1% SDS at 63° C.

VEGF-E mRNA was detectable in fetal lung, kidney, brain, and liver and in adult heart, placenta, liver, skeletal muscle, kidney, and pancreas. VEGF-E mRNA was also found in A549 lung adenocarcinoma and HeLa cervical adenocarcinoma cell lines.

Example 4

In situ Hybridization

In situ hybridization is a powerful and versatile technique for the detection and localization of nucleic acid sequences within cell or tissue preparations. It may be useful, for example, to identify sites of gene expression, analyze the tissue distribution of transcription, identify and localize viral infection, follow changes in specific mRNA synthesis, and aid in chromosome mapping.

In situ hybridization was performed following an optimized version of the protocol by Lu and Gillett, *Cell Vision* 1: 169-176 (1994), using PCR-generated $^{33}$P-labeled riboprobes. Briefly, formalin-fixed, paraffin-embedded human tissues were sectioned, deparaffinized, deproteinated in proteinase K (20 g/ml) for 15 minutes at 37° C., and further processed for in situ hybridization as described by Lu and Gillett, supra. A ($^{33}$-P)UTP-labeled antisense riboprobe was generated from a PCR product of 980 bp (using the oligonucleotide primers indicated below) and hybridized at 55° C. overnight. The slides were dipped in KODAK NTB2T™ nuclear track emulsion and exposed for 4 weeks.

$^{33}$P-Riboprobe Synthesis 6.0 µl (125 mCi) of $^{33}$P-UTP (Amersham BF 1002, SA<2000 Ci/mmol) were speed-vacuum dried. To each tube containing dried $^{33}$P-UTP, the following ingredients were added:

2.0 µl 5× transcription buffer
1.0 µl DTT (100 mM)
2.0 µl NTP mix (2.5 mM: 10 µl each of 10 mM GTP, CTP & ATP +10 µl $H_2O$)
1.0 µl UTP (50 µM)
1.0 µl RNAsin
1.0 µl DNA template (1 µg)
1. 0 µl $H_2O$
1.0 µl RNA polymerase (for PCR products T3=AS, T7=S, usually)

The tubes were incubated at 37° C. for one hour. A total of 1.0 µl RQ1 DNase was added, followed by incubation at 37° C. for 15 minutes. A total of 90 µl TE (10 mM Tris pH 7.6/1 mM EDTA pH 8.0) was added, and the mixture was pipetted onto DE81 paper. The remaining solution was loaded in a MICROCON-50™ ultrafiltration unit, and spun using program 10 (6 minutes). The filtration unit was inverted over a second tube and spun using program 2 (3 minutes). After the final recovery spin, a total of 100 µl TE was added. Then 1 µl of the final product was pipetted on DE81 paper and counted in 6 ml of BIOFLUOR II™.

The probe was run on a TBE/urea gel. A total of 1-3 µl of the probe or 5 µl of RNA Mrk III was added to 3 µl of loading buffer. After heating on a 95° C. heat block for three minutes, the gel was immediately placed on ice. The wells of gel were flushed, and the sample was loaded and run at 180-250 volts for 45 minutes. The gel was wrapped in plastic wrap (SARAN™ brand) and exposed to XAR film with an intensifying screen in a −70° C. freezer one hour to overnight.

$^{33}$P-Hybridization

A. Pretreatment of Frozen Sections

The slides were removed from the freezer, placed on aluminum trays, and thawed at room temperature for 5 minutes. The trays were placed in a 55° C. incubator for five minutes to reduce condensation. The slides were fixed for 10 minutes in 4% paraformaldehyde on ice in the fume hood, and washed in 0.5×SSC for 5 minutes, at room temperature (25 ml 20×SSC +975 ml s.c. $H_2O$). After deproteination in 0.5 µg/ml proteinase K for 10 minutes at 37° C. (12.5 µl of 10 mg/ml stock in 250 ml prewarmed RNAse-free RNAse buffer), the sections were washed in 0.5×SSC for 10 minutes at room temperature. The sections were dehydrated in 70%, 95%, and 100% ethanol, 2 minutes each.

B. Pretreatment of Paraffin-embedded Sections

The slides were deparaffinized, placed in s.c. $H_2O$, and rinsed twice in 2×SSC at room temperature, for 5 minutes each time. The sections were deproteinated in 20 µg/ml proteinase K (500 µl of 10 mg/ml in 250 ml RNAse-free RNAse buffer; 37° C., 15 minutes) for human embryo tissue, or 8× proteinase K (100 µl in 250 ml RNAse buffer, 37° C., 30 minutes) for formalin tissues. Subsequent rinsing in 0.5×SSC and dehydration were performed as described above.

C. Prehybridization

The slides were laid out in a plastic box lined with Box buffer (4×SSC, 50% formamide). The filter paper was saturated. The tissue was covered with 50 µl of hybridization buffer (3.75 g dextran sulfate+6 ml s.c. $H_2O$), vortexed, and heated in the microwave for 2 minutes with the cap loosened. After cooling on ice, 18.75 ml formamide, 3.75 ml 20×SSC, and 9 ml s.c. $H_2O$ were added, and the tissue was vortexed well and incubated at 42° C. for 1-4 hours.

D. Hybridization $1.0 \times 10^6$ cpm probe and 1.0 µl tRNA (50 mg/ml stock) per slide were heated at 95° C. for 3 minutes. The slides were cooled on ice, and 48 µl hybridization buffer was added per slide. After vortexing, 50 µl $^{33}$P mix was added to 50 µl prehybridization on the slide. The slides were incubated overnight at 55° C.

E. Washes

Washing was done for 2×10 minutes with 2×SSC, EDTA at room temperature (400 ml 20×SSC+16 ml 0.25 M EDTA, $V_f$=4L), followed by RNAseA treatment at 37° C. for 30 minutes (500 µl of 10 mg/ml in 250 ml RNAse buffer=20 µg/ml). The slides were washed 2×10 minutes with 2×SSC, EDTA at room temperature. The stringency wash conditions were as follows: 2 hours at 55° C., 0.1×SSC, EDTA (20 ml 20×SSC+16 ml EDTA, $V_f$=4L)

F. Oligonucleotide Primers

In situ analysis was performed on the DNA29101 sequence disclosed herein. The oligonucleotide primers employed to prepare the riboprobe for these analyses were as follows.

```
p1: 5'-GGA TTC TAA TAC GAC TCA CTA TAG GGC GGC GGA ATC CAA CCT GAG TAG    (SEQ ID NO:7)

p2  5'-CTA TGA AAT TAA CCC TCA CTA AAG GGA GCG GCT ATC CTC CTG TGC TC     (SEQ ID NO:8)
```

G. Results

The results from this in situ analysis were as follows.

For the lower human fetal limb, there was expression of VEGF-E in developing lower limb bones at the edge of the cartilagenous anlage (i.e., around the outside edge), in developing tendons, in vascular smooth muscle, and in cells embracing developing skeletal muscle myocytes and myotubes. Expression was also observed at the epiphyseal growth plate. There was human fetal lymph node expression of VEGF-E in the marginal sinus of developing lymph nodes. There was human fetal thymus expression in the subcapsular region of the thymic cortex, possibly representing either the subcapsular epithelial cells or the proliferating, double-negative thymocytes that are found in this region. The human fetal spleen was negative for expression.

Trachea expression of VEGF-E in the smooth muscle of human fetal tissue was observed. There was human fetal brain (cerebral cortex) focal expression of VEGF-E in cortical neurons. The human fetal spinal cord was negative. There was human fetal small intestine expression of VEGF-E in smooth muscle. In addition, there was human fetal thyroid generalized expression of VEGF-E over thryoid epithelium. The human fetal adrenal gland was negative. Liver expression of VEGF-E in human fetal ductal plate cells was observed, as well as human fetal stomach expression in mural smooth muscle and human fetal skin expression in basal layer of the squamous epithelium. In addition, there was human fetal placenta expression of VEGF-E in interstitial cells in trophoblastic villi, and human fetal cord expression in the wall of the arteries and veins.

When tested in superovulated rat ovaries, all sections, control and superovulated ovaries, were negative with both antisense and sense probes.

Either the message was not expressed in this model, or the human probe does not cross react with rat.

High expression of VEGF-E was observed at the following additional sites:

chimp ovary—granulosa cells of maturing follicles, lower intensity signal observed over thecal cells.
chimp parathyroid—high expression over chief cells.
human fetal testis—moderate expression over stromal cells surrounding developing tubules
human fetal lung—high expression over chondrocytes in developing bronchial tree, and low level expression over branching bronchial epithelium.

Specific expression was not observed over the renal cell, gastric and colonic carcinomas.

The fetal tissues examined in the above study (E12-E16 weeks) included: placenta, umbilical cord, liver, kidney, adrenals, thyroid, lungs, heart, great vessels, oesophagus, stomach, small intestine, spleen, thymus, pancreas, brain, eye, spinal cord, body wall, pelvis and lower limb.

The adult tissues examined in the above study included: liver, kidney, adrenal, myocardium, aorta, spleen, lymph node, pancreas, lung, skin, cerebral cortex (rm), hippocampus (rm), cerebellum (rm), penis, eye, bladder, stomach, gastric carcinoma, colon, colonic carcinoma, and chondrosarcoma, as well as tissues having acetominophen-induced liver injury, and hepatic cirrhosis.

In summary, the expression pattern suggests that VEGF-E may be involved in cell differentiation and/or proliferation. Expression patterns in developing skeletal muscle suggest that the protein may be involved in myoblast differentiation and/or proliferation.

Example 5

Myocyte Hypertrophy Assay

Myocytes from neonatal Harlan Sprague Dawley rat heart ventricle (23 days gestation) were plated in duplicate at 75000 cells/ml in a 96-well plate. Cells were treated for 48 h with 2000, 200, 20, or 2 ng/ml VEGF-E-IgG. Myocytes were stained with crystal violet to visualize morphology and scored on a scale of 3 to 7, 3 being nonstimulated and 7 being full-blown hypertrophy.

2000 ng/ml and 200 ng/ml VEGF-E caused hypertrophy, scored as a 5.

Example 6

Cell Proliferation Assay

Mouse embryonic fibroblast C3H10T1/2 cells (ATCC) were grown in 50:50 Ham's F-12: low glucose DMEM medium containing 10% fetal calf serum (FCS). Cells were plated in duplicate in a 24-well plate at 1000, 2000, and 4000 cells/well. After 48 hours, cells were switched to medium containing 2% FCS and were incubated for 72 hours with 200, 800, or 2000 ng/ml VEGF-E or no growth factor added.

Approximately 1.5 fold greater number of cells were measured in the presence of 200 ng/ml VEGF-E as in its absence, at all three cell densities.

Example 7

Endothelial Cell Survival Assay

Human umbilical vein endothelial cells (HUVEC, Cell Systems) were maintained in Complete Media (Cell Systems) and plated in triplicate in serum-free medium (Basic Media from Cell Systems containing 0.1% BSA) at 20,000 cells/well of a 48-well plate. Cells were incubated for 5 days with 200 or 400 ng/ml VEGF-E-IgG, 100 ng/ml VEGF, 20 ng/ml basic FGF, or no addition.

Survival was 2-3 times greater with VEGF-E as compared to lack of growth factor addition. VEGF and basic FGF were included as positive controls.

Example 8

Stimulation of Endothelial Tube Formation

This assay follows the assay described in Davis and Camarillo, *Experimental Cell Research*, 224:39-51 (1996), or one modified from it as follows:

Protocol: HUVEC cells (passage number less than 8 from primary) are mixed with type I rat tail collagen, final concentration 2.6 mg/ml at a density of $6 \times 10^5$ cells/ml and plated at 50 µl per well on a 96-well plate. The gel is allowed to solidify for 1 hr at 37° C., then 50 µl per well of M199 culture media supplemented with 1% FBS and a VEGF-E sample (at dilutions of 1%, 0.1%, and 0.01%, respectively) is added along with 1 µM 6-FAM-FITC dye to stain vacuoles while they are forming. Cells are incubated at 37° C./5% $CO_2$ for 48 hr, fixed with 3.7% formalin at room temperature for 10 minutes, washed with PBS five times, then stained with Rh-Phalloidin at 4° C. overnight followed by nuclear staining with 4 µM DAPI.

1. Apoptosis Assay

This assay will identify factors that facilitate cell survival in a 3-dimensional matrix in the presence of exogenous growth factors (VEGF, bFGF without PMA).

A positive result is equal to or less than 1. 0=no apoptosis, 1=less than 20% cells are apoptotic, 2=less than 50% cells are apoptotic, 3=greater than 50% cells are apoptotic. Stimulators of apoptosis in this system are expected to be apoptotic factors, and inhibitors are expected to prevent or lessen apoptosis.

2. Vacuoles Assay

This assay will identify factors that stimulate endothelial vacuole formation and lumen formation in the presence of bFGF and VEGF (40 ng/ml).

A positive result is equal to or greater than 2. 1=vacuoles present in less than 20% of cells, 2=vacuoles present in 20-50% of cells, 3=vacuoles present in greater than 50% of cells. This assay is designed to identify factors that are involved in stimulating pinocytosis, ion pumping, permeability, and junction formation.

3. Tube Formation Assay

This assay is to identify factors that stimulate endothelial tube formation in a 3-dimensional matrix. This assay will identify factors that stimulate endothelial cells to differentiate into a tube-like structure in a 3-dimensional matrix in the presence of exogenous growth factors (VEGF, bFGF).

A positive result is equal to or greater than 2. 1=cells are all round, 2=cells are elongated, 3=cells are forming tubes with some connections, 4=cells are forming complex tubular networks. This assay would identify factors that may be involved in stimulating tracking, chemotaxis, or endothelial shape change.

The results are shown in FIGS. 3 through 5. FIG. 3A shows the HUVEC tube formation when no growth factors are present. FIG. 3B shows where VEGF/bFGF, and PMA are present, FIG. 3C shows where VEGF and bFGF are present, FIG. 3D shows where VEGF and PMA are present, FIG. 3E shows where bFGF and PMA are present, FIG. 3F shows where VEGF is present, FIG. 3G shows where bFGF is present, and FIG. 3H shows where PMA is present.

Figure 4A:
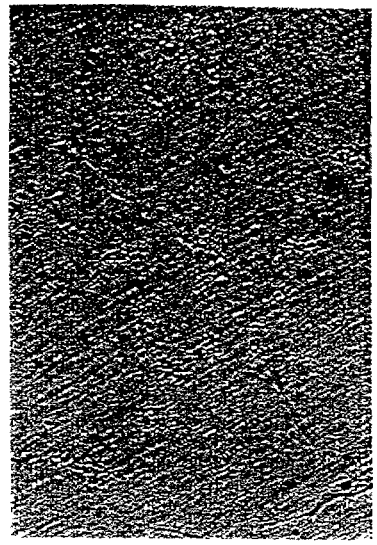
FIGS. 4A and 4B show, respectively, the effect on HUVEC tube formation of VEGF-E conjugated to IgG at 1% dilution and of a buffer control (10 mM HEPES/0.14M NaCl/4% mannitol, pH 6.8) at 1% dilution.
Figure 4B:
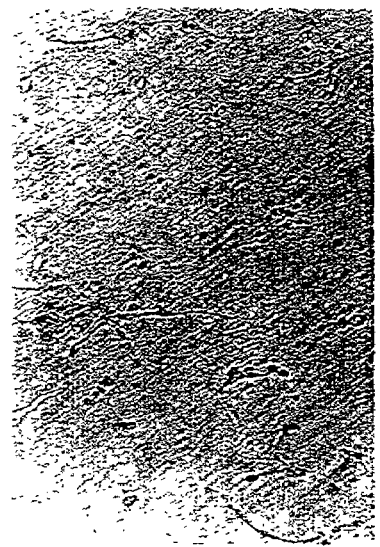
Figure 5A:
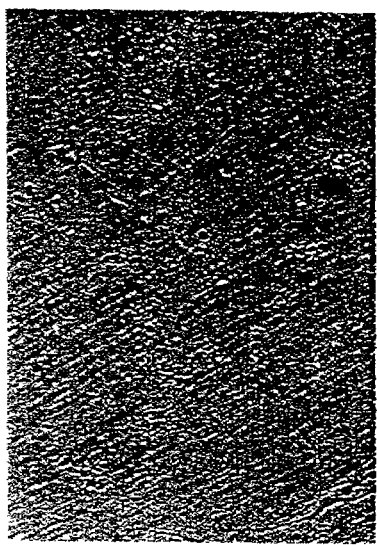
FIGS. 5A and 5B show, respectively, the effect on HUVEC tube formation of VEGF-E conjugated to poly-his at 1% dilution and of a buffer control (same as in FIG. 4B) at 1% dilution.
Figure 5B:
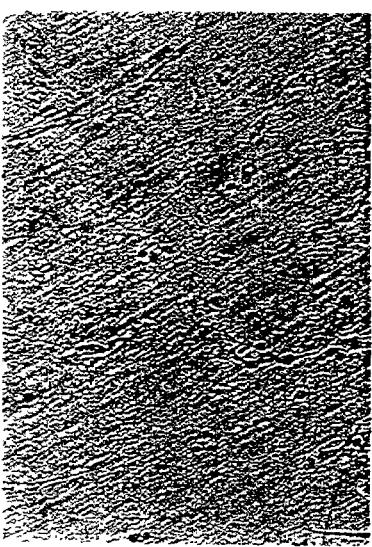

FIGS. 4A and 4B show, respectively, the effect on HUVEC tube formation of VEGF-E-IgG at 1% dilution and of a buffer control (10 mM HEPES/0.14M NaCl/4% mannitol, pH 6.8) at 1% dilution. FIGS. 5A and 5B show, respectively, the effect on HUVEC tube formation of VEGF-E-poly-his at 1% dilution and of the buffer control used for VEGF-E-IgG at 1% dilution.

The results clearly show more complex tube formation with the VEGF-E-IgG and VEGF-E-poly-his samples than with the buffer controls.

Example 9

Transgenic Mice

Transgenic mice were generated by microinjection of C57Bl/6/SJL F2 mouse embryos (DNAX) with a vector suitable for such microinjection containing the cDNA encoding VEGF-E under the control of a keratin promoter (Xie et al., *Nature*, 391: 90-92 (1998)), driving expression in the skin.

Transgenic pups were wrinkled and shiny at birth and were delayed in getting their hair. The mice lost their phenotype by two weeks of age. There were no detectable histopathic changes.

Example 10

Production of Antibodies

Polyclonal antisera were generated in female New Zealand White rabbits against human VEGF-E. The protein was homogenized with Freund's complete adjuvant for the primary injection and with Freund's incomplete adjuvant for all subsequent boosts. For the primary immunization and the first boost, 3.3 µg per kg body weight was injected directly into the popliteal lymph nodes, according to Bennett et al., *J. Biol. Chem.*, 266: 23060-23067 (1991); and "Production of Antibodies by Inoculation into Lymph Nodes" by Sigel, Sinha and VanderLaan in *Methods in Enzymology*, Vol. 93 (New York: Academic Press, 1983). For all subsequent boosts, 3.3 µg per kg body weight was injected into subcutaneous and intramuscular sites. Injections were done every 3 weeks with bleeds taken on the following 2 weeks after each injection. The polyclonal antisera thus obtained contained antibodies binding VEGF-E, as revealed by immunoprecipitation experiments.

Example 11

Inhibition of VEGF-stimulated Endothelial Cell (ACE Cells) Growth

Bovine adrenal cortical capillary endothelial cells (ACE cells) (from primary culture, maximum of 12-14 passages) were plated in 96-well plates at 500 cells/well per 100 microliter. Assay media included low glucose DMEM, 10% calf serum, 2 mM glutamine, and 1× penicillin/streptomycin/fungizone. Control wells included the following: (1) no ACE cells added; (2) ACE cells alone; (3) ACE cells plus 5 ng/ml FGF; (4) ACE cells plus 3 ng/ml VEGF; (5) ACE cells plus 3 ng/ml VEGF plus 1 ng/ml TGF-beta; and (6) ACE cells plus 3 ng/ml VEGF plus 5 ng/ml LIF. The test sample, poly-his tagged VEGF-E polypeptide (described in the Examples above; in 100 microliter volumes), was then added to the wells (at dilutions of 1%, 0.1% and 0.01%, respectively). The cell cultures were incubated for 6-7 days at 37° C./5% $CO_2$. After the incubation, the media in the wells was aspirated, and the cells were washed 1× with PBS. An acid phosphatase reaction mixture (100 microliter; 0.1M sodium acetate, pH 5.5, 0.1% Triton X-100, 10 mM p-nitrophenyl phosphate) was then added to each well. After a 2 hour incubation at 37° C., the reaction was stopped by addition of 10 microliters 1N NaOH. Optical density (OD) was measured on a microplate reader at 405 nm.

The activity of VEGF-E was calculated as the percent inhibition of VEGF (3 ng/ml) stimulated proliferation (as determined by the acid phosphatase activity at OD 405 nm) relative to the cells without stimulation. TGF-beta was employed as an activity reference—at 1 ng/ml, TGF-beta blocks 70-90% of VEGF-stimulated ACE cell proliferation. Results of the assay were interpreted as "positive" if the observed inhibition was ≧30%.

In a first assay run, the VEGF-E at 1%, 0.1%, and 0.01% dilutions exhibited 52%, 90% and 96% inhibition, respectively. In a second assay run, the VEGF-E at 1%, 0.1%, and 0.01% dilutions exhibited 57%, 93% and 91% inhibition, respectively.

Deposit of Material

The following material has been deposited with the American Type Culture Collection, 10801 University Blvd., Manassas, Va. USA (ATCC):

| Material | ATCC Dep. No. | Deposit Date |
| --- | --- | --- |
| DNA29101-1272 | 209653 | Mar. 5, 1998 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR □1.14 with particular reference to 886 OG 638).

The assignee of the present application has agreed that if a culture of the material on deposit should die or be lost or destroyed when cultivated under suitable conditions, the material will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated antibody that binds vascular endothelial cell growth factor-E (VEGF-E) polypeptide set forth in SEQ ID NO. 2.

2. The antibody of claim 1 that is a monoclonal antibody.

3. An article of manufacture, comprising:
a container;
a label on the container; and
a composition comprising the antibody of claim 1 contained within the container.

4. The antibody of claim 1 that is a polyclonal antibody.

5. The antibody of claim 1 that is a humanized antibody.

6. The antibody of claim 1 that is a human antibody.

7. A composition comprising the antibody of claim 1 and a pharmaceutical carrier.

* * * * *